United States Patent
Whitt et al.

(10) Patent No.: US 9,856,538 B2
(45) Date of Patent: Jan. 2, 2018

(54) METHODS AND COMPOSITIONS FOR ANALYZING AHASL GENES IN WHEAT

(71) Applicant: BASF Agrochemmical Products B.V., MC Arnhem (NL)

(72) Inventors: Sherry Whitt, Research Triangle Park, NC (US); Cory Rodgers, Research Triangle Park, NC (US)

(73) Assignee: BASF Agrochemical Products B.V., Arnhem (NL)

(*) Notice: Subject to any disclaimer, the term of this patent is extended or adjusted under 35 U.S.C. 154(b) by 45 days.

(21) Appl. No.: 14/364,982

(22) PCT Filed: Dec. 13, 2012

(86) PCT No.: PCT/US2012/069522
§ 371 (c)(1),
(2) Date: Jun. 12, 2014

(87) PCT Pub. No.: WO2013/090585
PCT Pub. Date: Jun. 20, 2013

(65) Prior Publication Data
US 2015/0056617 A1    Feb. 26, 2015

Related U.S. Application Data

(60) Provisional application No. 61/576,944, filed on Dec. 16, 2011, provisional application No. 61/650,912, filed on May 23, 2012.

(51) Int. Cl.
C12Q 1/68 (2006.01)
C07H 21/04 (2006.01)

(52) U.S. Cl.
CPC ..... C12Q 1/6895 (2013.01); *C12Q 2600/124* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS 7,432,082 B2 * 10/2008 Zhao ............... C12Q 1/6895
435/6.12
8,206,906 B2 *  6/2012 Zhao ............... C12Q 1/6895
435/6.1

(Continued)

FOREIGN PATENT DOCUMENTS

CL    3255-12        8/2013
JP    2007/082429 A  4/2007

(Continued)

OTHER PUBLICATIONS

Newton (Nucleic Acid Research, vol. 17, No. 7, pp. 2503-2516, 1989).*

(Continued)

*Primary Examiner* — Jeanine A Goldberg
(74) *Attorney, Agent, or Firm* — Mintz Levin Cohn Ferris Glovsky and Popeo, P.C.

(57) ABSTRACT

The present disclosure provides methods, kits, and primers for analyzing AHASL genes of plants, including wheat. The methods, kits, and primers of the present disclosure can make use of forward AHASL primers designed without use of software or other assay-design technology and can be used in a real-time PCR assay to determine the zygosity of AHASL genes encoding AHAS enzymes providing tolerance to AHAS enzyme inhibitors.

23 Claims, 8 Drawing Sheets

(56) References Cited

U.S. PATENT DOCUMENTS

| | | | |
|---|---|---|---|
| 8,877,911 B2* | 11/2014 | Zhao | C12Q 1/6895 435/6.1 |
| 2006/0010514 A1 | 1/2006 | Birk et al. | |
| 2006/0070137 A1 | 3/2006 | Rommens et al. | |
| 2008/0096766 A1* | 4/2008 | Lee | C12Q 1/6851 506/6 |

FOREIGN PATENT DOCUMENTS

| WO | WO 01/92512 | 12/2001 |
|---|---|---|
| WO | WO2004/106529 A2 | 12/2004 |
| WO | WO 2005/093093 A2 | 10/2005 |
| WO | WO2007/140451 A1 | 12/2007 |
| WO | WO 2010/080829 A1 | 7/2010 |

OTHER PUBLICATIONS

Anderson et al., "Resistance to an imidazolinone herbicide is conferred by a gene on chromosome 6DL in the wheat line cv. 9804", Weed Science, Jan. 1, 2004 (Jan. 1, 2004), vol. 52, pp. 83-90.

Pozniak et al., "Physiological and Molecular Characterization of Mutation-Derived Imidazolinone Resistance in Spring Wheat", Crop Science, Jul. 1, 2004 (Jul. 7, 2004). vol. 44, No. 4 pp. 1434-1443.

International Search Report for PCT/US2012/069522 dated Jun. 19, 2013.

D. Li et al., "A mutation at the Ala122 position of acetohydroxyacid synthase (AHAS) located on chromosome 6D of wheat: improved resistance to imidazolinone and a faster assay for marker assisted selection," Molecular Breeding, vol. 22, No. 2, pp. 217-225, Mar. 21, 2008.

Rodriguez-Suarez C. et al., "Selection and molecular characterization of imidazolinone resistant mutation-derived lines of Tritordeum HT621," Molecular Breeding, vol. 23, No. 4, pp. 565-572, Jan. 20, 2009.

Alejandro Perez-Jones et al., "Introgression of an imidazolinone-resistance gene from winter wheat (*Triticum aestivum* L.) into jointed goatgrass (Aegilops cylindrical Host)," Theoretical and Applied Genetics, International Journal of Plant Breeding Research, vol. 114, No. 1, pp. 177-186, Oct. 21, 2006.

Cheryl-Ann L. Corbett et al., "Detection of resistance to acetolactate synthase inhibitors in weeds with emphasis on DNA-based techniques: a review", Pest Management Science, vol. 62, No. 7, pp. 584-597, Jul. 1, 2006.

Supplemental European Search Report from EP 12 85 7037 dated Jun. 23, 2015.

* cited by examiner

FIG. 1

A  *AHASL1D*

WT

```
CACGTGCTGCCTATGATCCCAAGCGGTGGTGCTTTCAAGGAC
 H   V   L   P   M   I   P   S   G   G   A   F   K   D
```

MUT

```
CACGTGCTGCCTATGATCCCAAACGGTGGTGCTTTCAAGGAC
 H   V   L   P   M   I   P   N   G   G   A   F   K   D
```

B  *AHASL1B*

WT

```
CACGTGCTGCCTATGATCCCAAGCGGTGGTGCTTTTAAGGAC
 H   V   L   P   M   I   P   S   G   G   A   F   K   D
```

MUT

```
CACGTGCTGCCTATGATCCCAAACGGTGGTGCTTTTAAGGAC
 H   V   L   P   M   I   P   N   G   G   A   F   K   D
```

C  *AHASL1A*

WT

```
CACGTGCTGCCTATGATCCCAAGCGGTGGTGCTTTCAAGGAC
 H   V   L   P   M   I   P   S   G   G   A   F   K   D
```

MUT

```
CACGTGCTGCCTATGATCCCAAACGGTGGTGCTTTCAAGGAC
 H   V   L   P   M   I   P   N   G   G   A   F   K   D
```

FIG. 3

| | Hexaploid L1D | Hexaploid L1B | Hexaploid L1A | Tetraploid L1B | Tetraploid L1A |
|---|---|---|---|---|---|
| Hexaploid L1D | 100% | | | | |
| Hexaploid L1B | | 100% | | | |
| Hexaploid L1A | | | 100% | | 97.8% |
| Tetraploid L1B | | | | 100% | 97.3% |
| Tetraploid L1A | | | | 97.3% | 100% |

FIG. 7A

```
» AHASL1B  (1251)  TTTGGTCCATGGCACAAGGAGTTGGATCAGCAGAAGAGGGAGTTTCCTCT
» AHASL1D  ( 945)  TTTGGTCCATGGCACAAGGAGTTGGATCAGCAGAAGAGGGAGTTTCCTCT
» AHASL1A  (1058)  TTTGGTCCATGGCACAAGGAGTTGGATCAGCAGAAGAGGGAGTTTCCTCT
                  (1251)

» AHASL1B  (1301)  AGGATTCAAGACTTTTGGTGAGGCCATCCCGCCGCAATATGCTATCCAGG
» AHASL1D  ( 995)  AGGATTCAAGACTTTTGGCGAGGCCATCCCGCCGCAATATGCTATCCAGG
» AHASL1A  (1108)  AGGATTCAAGACTTTTGGCGAGGCCATCCCGCCGCAATATGCTATCCAGG
                  (1301)

» AHASL1B  (1351)  TACTGGATGAGCTGACAAAAGGGAGGCGATCATTGCCACCGGTGTTGGG
» AHASL1D  (1045)  TACTGGATGAGCTGACAAAAGGGAGGCGATCATTGCCACTGGTGTTGGG
» AHASL1A  (1158)  TACTGGATGAGCTGACAAAAGGGAGGCGATCATTGCTACTGGTGTTGGG
                  (1351)

» AHASL1B  (1401)  CAGCATCAGATGTGGGCGGCTCAGTATTACACTTACAAGCGGCCACGGCA
» AHASL1D  (1095)  CAGCACCAGATGTGGGCGGCTCAGTATTACACTTACAAGCGGCCACGGCA
» AHASL1A  (1208)  CAGCACCAGATGTGGGCGGCTCAGTATTACACTTACAAGCGGCCACGGCA
                  (1401)

» AHASL1B  (1451)  GTGGCTGTCTTCATCCGGTTTGGGTGCAATGGGATTTGGGTTGCCAGCTG
» AHASL1D  (1145)  GTGGCTGTCTTCGTCTGGTTTGGGGGCAATGGGATTTGGGTTACCAGCTG
» AHASL1A  (1258)  GTGGCTGTCTTCGTCTGGTTTGGGGGCAATGGGATTTGGGTTACCAGCTG
                  (1451)

» AHASL1B  (1501)  CAGCTGGCGCTGCTGTGGCCAACCCAGGTGTTACAGTTGTTGACATTGAT
» AHASL1D  (1195)  CAGCTGGCGCTGCTGTGGCCAACCCAGGTGTTACAGTTGTTGACATTGAT
» AHASL1A  (1308)  CAGCTGGCGCTGCTGTGGCCAACCCAGGTGTTACAGTTGTTGACATTGAT
                  (1501)

» AHASL1B  (1551)  GGGGATGGTAGTTTCCTCATGAACATTCAGGAGTTGGCGTTGATCCGTAT
» AHASL1D  (1245)  GGTGATGGTAGTTTCCTCATGAACATTCAGGAGTTGGCGTTGATCCGCAT
» AHASL1A  (1358)  GCAGATGGTAGTTTCCTCATGAACATTCAGGAGTTGGCATTGATCCGTAT
                  (1551)

» AHASL1B  (1601)  TGAGAACCTCCCAGTGAAGGTGATGATATTGAACAACCAGCATCTGGGAA
» AHASL1D  (1295)  TGAGAACCTCCCAGTGAAGGTGATGATATTGAACAACCAGCATCTGGGAA
» AHASL1A  (1408)  TGAGAACCTCCCTGTGAAGGTGATGATATTGAACAACCAGCATCTGGGAA
                  (1601)
```

FIG. 7B

```
» AHASL1B  (1651)  TGGTGGTGCAGTGGGAGGATAGGTTTTACAAGGCCAACCGGGCGCACACA
» AHASL1D  (1345)  TGGTGGTGCAGTGGGAGGATAGGTTTTACAAGGCCAATCGGGCGCACACA
» AHASL1A  (1458)  TGGTGGTGCAATGGGAGGATAGGTTTTACAAGGCCAATCGGGCGCACACA
                  (1651)

» AHASL1B  (1701)  TACCTTGGCAACCCAGAAAATGAGAGTGAGATATATCCAGATTTTGTGAC
» AHASL1D  (1395)  TACCTTGGCAACCCAGAAAATGAGAGTGAGATATATCCAGATTTTGTGAC
» AHASL1A  (1508)  TACCTTGGCAACCCAGAAAATGAGAGTGAGATATATCCAGATTTTGTGAC
                  (1701)

» AHASL1B  (1751)  GATTGCTAAAGGATTCAACGTTCCGGCAGTTCGTGTGACGAAGAAGAGCG
» AHASL1D  (1445)  GATTGCTAAAGGATTCAACGTTCCAGCAGTTCGAGTGACGAAGAAGAGCG
» AHASL1A  (1558)  GATTGCTAAAGGATTCAACGTTCCGGCAGTTCGTGTGACGAAGAAGAGCG
                  (1751)

» AHASL1B  (1801)  AAGTCACTGCAGCAATCAAGAAGATGCTTGAGACCCCAGGGCCATACTTG
» AHASL1D  (1495)  AAGTCACTGCAGCAATCAAGAAGATGCTTGAGACCCCAGGGCCATACTTG
» AHASL1A  (1608)  AAGTCACTGCAGCAATCAAGAAGATGCTTGAGACCCCAGGGCCATACTTG
                  (1801)

» AHASL1B  (1851)  TTGGATATCATTGTCCCGCATCAGGAGCACGTGCTGCCTATGATCCCAAG
» AHASL1D  (1545)  TTGGATATCATAGTCCCGCATCAGGAGCACGTGCTGCCTATGATCCCAAG
» AHASL1A  (1658)  TTGGATATCATCGTCCCGCATCAGGAGCACGTGCTGCCTATGATCCCAAG
                  (1851)

» AHASL1B  (1901)  CGGTGGTGCTTTTAAGGACATGATCATGGAGGGTGATGGCAGGACCTCGT
» AHASL1D  (1595)  CGGTGGTGCTTTCAAGGACATGATCATGGAGGGTGATGGCAGGACCTCGT
» AHASL1A  (1708)  CGGTGGTGCTTTCAAGGACATGATCATGGAGGGTGATGGCAGGACCTCGT
                  (1901)

» AHASL1B  (1951)  ACTGAAATTTCGACCTACAAGACCTACAAGTGTGACATGCGCAATCAGCA
» AHASL1D  (1645)  ACTGAAATTTCGACCTACAAGACCTACAAGTGTGACATGCGCAATCAGCA
» AHASL1A  (1758)  ACTGAAATTTCGACCTACAAGACCTACAAGTGTGACATGCGCAATCAGCA
                  (1951)

» AHASL1B  (2001)  TGATACCTGCGTGTTGTATCAACTACTGGGGGTTCAACTGTGAACCATGC
» AHASL1D  (1695)  TGATGCCCGCGTGTTGTATCAACTACTAGGGGTTCAACTGTGAACCATGC
» AHASL1A  (1808)  TGGTGCCCGCGTGTTGTATCAACTACTAGGGGTTCAACTGTGAACCATGC
                  (2001)

» AHASL1B  (2051)  GTTTTCTAGTTTGCTTGTTTCATTCATATAAGCTTGTGTTACTTAGTTCC
» AHASL1D  (1745)  GTTTTCTAGTTTGCTTGTTTCATTCATATAAGCTTGTRTTACTTAGTTCC
» AHASL1A  (1858)  GTTTTCTAGTTTGCTTGTTTCATTCATATAAGCTTGTGTTACTTAGTTCC
                  (2051)
```

FIG. 7C

```
» AHASL1B  (2101) GAACCGTGTAGTTTTGTAGTCTCTGTTCTCTTTTGTAGGGAYGTGCTGTC
» AHASL1D  (1795) GAACCCTGTAGTTTTGTAGTCTATGTTCTCTTTTGTAGGGATGTGCTGTC
» AHASL1A  (1908) GAACCCTGTAGCTTTGTAGTCTATGCTATCTTTTGTAGGGATGTGCTGTC
                 (2101)

» AHASL1B  (2151) ATAARATATCATGCAAGTTTCTTGTCCTACATATCAATAATAAGCACTTC
» AHASL1D  (1845) ATAARATRTCATGCAAGTTTCTTGTCCTACATATCAATAATAAGTACTTC
» AHASL1A  (1958) ATAARATATCATGCAAGTTTCTTGTCCTACATATCAATAATAAGTACTTC
                 (2151)

» AHASL1B  (2201) CATGGAGCAAAAAAAAAAAAAAAAAAAAAAAAAA
» AHASL1D  (1895) CATGCAGTAAAAAAAAAAAAAAAAAAAAAAAAAA
» AHASL1A  (2008) CATGGAAAAAAAAAAAAAAAAAAAAAAAAAAAAA
                 (2201)
```

METHODS AND COMPOSITIONS FOR ANALYZING AHASL GENES IN WHEAT

CROSS-REFERENCE TO RELATED APPLICATIONS

This application is a U.S. National Stage application of PCT/US2012/069522, which claims priority to U.S. Provisional Application for Patent Ser. No. 61/576,944 filed Dec. 16, 2011, and U.S. Provisional Application for Patent Ser. No. 61/650,912 filed May 23, 2012, the disclosures of which are incorporated herein by reference in their entirety.

FIELD OF INVENTION

The present disclosure relates to the field of gene analysis and, particularly, to methods and compositions for the analysis of AHASL genes and indentifying the zygosity of the same.

BACKGROUND OF INVENTION

Acetohydroxyacid synthase (AHAS; EC 4.1.3.18), also known as acetolactate synthase (ALS), is the first enzyme that catalyzes the biochemical synthesis of the branched-chain amino acids valine, leucine, and isoleucine (Singh B. K. (Ed) *Plant amino acids*. Marcel Dekker Inc. New York, N.Y. Pg 227-247). AHAS is the site of action of four structurally diverse herbicide families including the sulfonylureas (LaRossa R A and Falco S C, 1984 *Trends Biotechnol.* 2:158-161), the imidazolinones (Shaner et al., 1984 *Plant Physiol.* 76:545-546), the triazolopyrimidines (Subramanian and Gerwick, 1989, Inhibition of acetolactate synthase by triazolopyrimidines in (ed) Whitaker J R, Sonnet P E *Biocatalysis in agricultural biotechnology*. ACS Symposium Series, American Chemical Society. Washington, D.C. Pg 277-288), and the pyrimidinylbenzoates (Subramanian et al., 1990 *Plant Physiol* 94: 239-244.). By inhibiting AHAS activity, these families of herbicides prevent further growth and development of susceptible plants, including many weed species. Imidazolinone (IMI) and sulfonylurea (SU) herbicides are widely used in modern agriculture due to their effectiveness at very low application rates and relative non-toxicity in animals.

In plants, the AHAS enzyme is comprised of two subunits: a large subunit (catalytic role) and a small subunit (regulatory role) (Duggleby and Pang (2000) J. Biochem. Mol. Biol. 33:1-36). The AHAS large subunit (AHASL) can be encoded by a single gene, as in the case of *Arabidopsis* and rice, or by multiple gene family members, as in maize, canola, and cotton. Specific, single-nucleotide substitutions in the large subunit can confer upon the enzyme a degree of insensitivity to one or more classes of herbicides (Chang and Duggleby (1998) Biochem J. 333:765-777). By convention, modifications of the AHAS amino acid sequence are typically identified in reference to their position in the *Arabidopsis thaliana* AHAS sequence (EMBL Accession No. X51514) and denoted with (At).

Modifications of AHAS genes can result in herbicide tolerant phenotypes (Hattori, 1995; Warwick, 2008). Substitutions in genes encoding the AHAS large subunit, which are referred to herein as AHASL genes, are the molecular basis of herbicide tolerance in CLEARFIELD® crops, which have increased tolerance to imidazolinone herbicides. Because each of these substitutions results in a semi-dominant phenotype, one substitution in a heterozygous state may be sufficient to produce a level of herbicide tolerance that is acceptable for many crop productions systems. However, for particular herbicide applications, and in cases with crop plants having multiple AHASL genes such as wheat, combinations of substitutions are desired to achieve an increased level of tolerance to herbicides.

*Triticum aestivum* is a hexaploid wheat species having three genomes, i.e., termed a D genome, a B genome, and an A genome. Each genome contains an AHAS gene and the genes have been named to take into account genome of origin and evolutionary relatedness, for example the AHAS large subunit gene located on the D, B, and A genomes of *Triticum aestivum* are referred to as TaAHASL1D, TaAHASL1B, and TaAHASL1A, respectively.

Each of the genes exhibit significant expression based on herbicide response and biochemical data from variants in each of the three genes (Ascenzi et al. (2003) International Society of Plant Molecular Biologists Congress, Barcelona, Spain, Ref. No. S10-17). The coding sequences of all three genes share extensive homology at the nucleotide level (WO 03/014357). Through sequencing the AHASL genes from several varieties of *Triticum aestivum*, the molecular basis of herbicide tolerance in most imidazolinone (IMI)-tolerant lines was found to be a single base pair change that results in the amino acid substitution S653(At)N (S653N), indicating a serine to asparagine substitution at a position equivalent to the serine at amino acid 653 in *Arabidopsis thaliana* (WO 03/014356; WO 03/014357). The S653N substitution is due to a single nucleotide polymorphism (SNP) in the DNA sequence encoding the AHASL protein. The substitution has been identified in all three genomes and must be easily and quickly distinguished for accurate breeding and confirmation of commercial seed lots (Berard, 2009; Dong, 2009).

One goal of plant breeders is to introduce imidazolinone tolerance into existing wheat lines by inducing the S653N substitution in the existing lines or by crossing non-IMI-tolerant lines with IMI-tolerant lines followed by backcrossing and selection for imidazolinone tolerance. Another goal of plant breeders is to produce wheat plants with increased levels of imidazolinone tolerance, beyond the levels of tolerance seen in wheat plants possessing a single S653N substitution in a single wheat AHASL gene. Thus, it is desirable to breed wheat plants that possess combinations of S653N substitutions at two or more of the AHASL genes. In addition, it is also desirable to breed wheat plants that are homozygous for the substituted S653N allele at one or more of the AHASL genes. However, to develop the desired wheat plants, rapid methods for identifying the desired plants are needed. Existing methods of detecting wheat plants with imidazolinone tolerance are not highly efficient for use in the development of plants that possess more than a single S653N allele at a single AHASL gene.

Existing methods of identifying plants with enhanced imidazolinone tolerance include field or greenhouse herbicide spray tests and biochemical assays for AHAS activity. However, such methods are time consuming and generally not suited for distinguishing, among large numbers of individual plants, subtle increases in imidazolinone tolerance that may occur when a second S653N allele is introduced into a wheat plant.

Alternative methods for identifying desired plants include DNA-based methods. For example, the AHASL genes, or portions thereof, can be amplified from genomic DNA by polymerase chain reaction (PCR) methods and the resulting amplified AHSL gene or portion thereof can be sequenced to identify the substituted S653N allele and the particular AHASL gene that it is present in. However, such a DNAsequencing-based method is not efficient for large numbers of samples. Another approach involves that use of radiolabelled or non-isotopically tagged, allele-specific oligonucleotides (ASOs) as probes for dot blots of genomic DNA or polymerase chain reaction (PCR) amplified DNA (Connor et al. (1983) Proc. Natl. Acad. Sci. USA 80:278-282; Orkin et al. (1983) J. Clin. Invest. 71:775-779; Brun et al. (1988) Nucl. Acids Res. 16:352; and Bugawan et al. (1988) Biotechnology 6:943-947. While such an approach is useful for distinguishing between two alleles at a single locus, this approach is not useful for the wheat AHASL genes, because three AHASL genes are nearly identical in the region surrounding the SNP that gives rise to the substituted S653(At)N AHASL protein. Thus, a set of six such oligonucleotide probes could not be developed that would be able to distinguish between the substituted and wild-type alleles at each of the three wheat AHASL genes.

One method that can be adapted for rapidly screening large numbers of individuals for the analysis of an SNP is the amplification refractory mutation system (ARMS) (Newton et al. (1989) Nucl. Acids Res. 17:2503-2516). This PCR-based method can be used to distinguish two alleles of a gene that differ by a single nucleotide and can also be used to distinguish heterozygotes from homozygotes for either allele by inspection of the PCR products after agarose gel electrophoresis and ethidium-bromide staining. The ARMS method is based on the premise that oligonucleotides with a mismatched 3'-residue will not function as primers in PCR under the appropriate conditions (Newton et al. (1989) Nucl. Acids Res. 17:2503-2516). An amplification-refractory mutation system (ARMS-PCR) using agarose-based gel detection methods may incorporate an internal nucleotide mismatch within an allele-specific (AS) primer to enhance the specificity of the assay. For example, the position of an internal mismatch was investigated in a multiple allelic system in a chicken population where the optimum primer had a mismatch 2 base pairs from the polymorphic nucleotide.

The usage of deliberate mismatches in quantitative PCR (qPCR) has been tested in the medical field. Single nucleotide polymorphism (SNP) genotyping is commonly performed to assess disease susceptibility and chimerism assessment. Development of one qPCR system has been attempted for monitoring chimerism. The SNP-specific qPCR assay was able to detect the positive template allele at 0.1%. The AS primers contained one to two intentional mismatches within 1-4 base pairs of the polymorphism of interest.

Mismatches in primers targeting a polymorphic region of a gene in a non-polyploid organism have been found to create a shift in the $C_T$ towards higher values during qPCR with SYBR-green detection (for example, the lim1 gene of *Picea glauca*.) This reduces assay sensitivity making this technique inadequate for pooled samples. The shift is less dramatic when the mismatch is located closer to the 3' end of the primer. However, it is necessary to decrease the DNA concentration in order to avoid voluntary addition of mismatches.

While ARMS-PCR has proven useful for the analysis of a SNP at a single gene, whether this method, or any other PCR-based methods, can be used be used for the analysis of SNPs that gives rise to herbicide-tolerant substitutions in native AHAS genes in different genomes of the same species, for example, the S653N substitution in each of the three wheat AHASL genes has not been reported. Existing methods experience a lack of assay sensitivity which can make them undesirable for SNP detection, particularly for SNP detection in and analysis of highly homologous genes in the same species, for example, in species having multiple genomes.

Thus, there remains a need for a method which can more efficiently distinguish between wheat plants having wild-type AHASLs and wheat plants having variant AHASLs and the zygosity of the same.

SUMMARY OF THE INVENTION

The present disclosure provides methods for analyzing a plant AHASL gene. The methods can involve an assay comprising providing DNA comprising the AHASL plant gene; amplifying the DNA using an AHASL forward primer, an AHASL reverse primer, polymerase, and deoxyribonucleotide triphosphates; detecting products of the amplification with a wild-type AHASL probe and a herbicide-tolerant AHASL probe to identify the zygosity of the AHASL gene, e.g., as homozygous wild-type, heterozygous, or homozygous substituted for the nucleotide substitution producing the S653N substitution. The assay can be a real-time PCR assay or a multiplex assay, including a multiplex real-time PCR assay. The wild-type AHASL probe can be labeled with a first type of detectable signal, for example, a first type of fluorescent reporter molecule and the herbicide-tolerant AHASL probe can be labeled with a second type of detectable signal, for example, a second type of fluorescent reporter molecule. The zygosity of the AHASL gene can be identified based on the dCt values generated during the real-time PCR assay.

The methods for analyzing a plant AHASL gene can be used to analyze genomic DNA. The methods can be used for analyzing the AHASL genes of plants having multiple genomes. For example, the methods described herein can be used to analyze AHASL genes of wheat plants, including hexaploid and tetraploid wheat plants, such as *Triticum aestivum* and *T. turgidum* ssp. *durum*, respectively.

It is desirable to have a method for distinguishing between AHASL genes of different wheat species. It is also desirable to have an assay that does not have a decrease in sensitivity when analyzing highly homologous genes within the same species, for example, plant species such as wheat that have multiple genomes which are highly similar. As described above, existing methods have decreased sensitivity and are unsuitable for these purposes. The methods described herein addresses lack of assay sensitivity of existing methods and permits distinguishing between AHASL genes of different wheat species and analyzing highly homologous genes within the same species, for example, *Triticum aestivum* and *T. turgidum* ssp. *durum*.

The methods disclosed herein make use of manually designed AHASL forward primers. Each of the AHASL forward primers can incorporate, as the 3'-terminal nucleotide, a nucleotide matching a triallelic single nucleotide polymorphism located approximately 40 nucleotides upstream from the nucleotide substitution in the AHASL gene producing the S653N substitution. The AHASL forward primer can also include one or more additional deliberate nucleotide mismatches with the AHASL gene. The deliberate mismatch can be located 2 or 3 nucleotides upstream from the 3'-terminal nucleotide of the AHASL forward primer. Thus, the AHASL forward primers can have a deliberate nucleotide mismatch with the nucleotide in the AHASL gene located 2 or 3 nucleotides upstream from the triallelic SNP.

As discussed above, the usage of primers with internal nucleotide mismatches can reduce assay sensitivity. The methods disclosed herein utilize primer designs based on a deliberate nucleotide mismatch and a unique polymorphism and real-time SNP genotyping for the trait of interest. Additionally, other types of markers, for example, insertions, deletions, di- or tri-nucleotide repeat, small microsatellite, or other SNPs, in the vicinity of the target polymorphism can provide a unique feature that can be used to increase assay specificity. The other types of markers can be located within 300 base pairs upstream or downstream of the target polymorphism, preferably within 200 base pairs, more preferably within 200 base pairs.

The methods as disclosed herein can use AHASL forward primers comprising the ten to fifteen terminal nucleotides of SEQ ID NO:13, SEQ ID NO:14, or SEQ ID NO:17. The AHASL forward primers can be selected from oligonucleotides having a sequence as set forth in SEQ ID NO:13, oligonucleotides having a sequence as set forth in SEQ ID NO:14, oligonucleotides having a sequence as set forth in SEQ ID NO:15, oligonucleotides having a sequence as set forth in SED ID NO:16, oligonucleotides having a sequence as set forth in SED ID NO:17, oligonucleotides having a sequence as set forth in SED ID NO:18, oligonucleotides having a sequence as set forth in SEQ ID NO: 19, oligonucleotides having a sequence as set forth in SED ID NO:20; oligonucleotides having a sequence as set forth in SED ID NO:21, oligonucleotides having a sequence as set forth in SED ID NO:22, oligonucleotides having a sequence as set forth in SED ID NO:23, oligonucleotides having a sequence as set forth in SEQ ID NO:24, oligonucleotides having a sequence as set forth in SEQ ID NO:25, oligonucleotides having a sequence as set forth in SEQ ID NO:26, oligonucleotides having a sequence as set forth in SEQ ID NO:27, oligonucleotides having a sequence as set forth in SEQ ID NO:28, and oligonucleotides having a sequence as set forth in SEQ ID NO:29.

The present disclosure also provides a kit for analyzing a plant AHASL gene. The kit can comprise an AHASL forward primer; a reverse AHASL primer; a wild-type AHASL probe; a herbicide-tolerant AHASL probe; a polymerase; and deoxyribonucleotide triphosphates.

The present disclosure also provides AHASL forward primers. The forward primers can be oligonucleotides having a sequence as set forth in SEQ ID NO:13, oligonucleotides having a sequence as set forth in SEQ ID NO:14, oligonucleotides having a sequence as set forth in SEQ ID NO:15, oligonucleotides having a sequence as set forth in SED ID NO:16, oligonucleotides having a sequence as set forth in SEQ ID NO:17, oligonucleotides having a sequence as set forth in SED ID NO:18; oligonucleotides having a sequence as set forth in SED ID NO:19, oligonucleotides having a sequence as set forth in SED ID NO:20, oligonucleotides having a sequence as set forth in SED ID NO:21, oligonucleotides having a sequence as set forth in SEQ ID NO:22, oligonucleotides having a sequence as set forth in SEQ ID NO:23, oligonucleotides having a sequence as set forth in SEQ ID NO:24, oligonucleotides having a sequence as set forth in SEQ ID NO:25, oligonucleotides having a sequence as set forth in SEQ ID NO:26, oligonucleotides having a sequence as set forth in SEQ ID NO:27, oligonucleotides having a sequence as set forth in SEQ ID NO:28, and oligonucleotides having a sequence as set forth in SEQ ID NO:29.

The present disclosure also provides AHASL probes, for example, probes which can be specific for a wild-type AHASL allele or a herbicide-tolerant AHASL allele. An exemplary wild-type probe sequence is given in SEQ ID NO:32. An exemplary herbicide-tolerant probe sequence is given in SEQ ID NO:33.

Described herein are AHASL probes useful in a multiplex format of the methods disclosed herein. A set of such probes can include two or three different probes incorporating as their 5'-end nucleotides different SNP nucleotides chosen from among the novel triallelic AHASL gene SNPs disclosed herein, and as their 3'-end nucleotides the nucleotide giving rise to the S653N substitution; and can include at least one "wild-type" probe also having such a SNP nucleotide as its 5'-end nucleotide, but having as its 3'-end nucleotide the wild-type nucleotide at the position corresponding to position 653 (At) of the AHASL gene. For example, a multiplex assay can make use of probes specific for each AHASL allele, such as a set of six probes, one for each of the wild-type and herbicide-tolerant alleles of AHASL1D, AHASL1B, and AHASL1A, wherein the probe for each allele is labeled with a unique detectable signal permitting detection of all AHASL alleles present in a sample.

BRIEF DESCRIPTION OF THE DRAWINGS

FIG. 1A depicts the partial nucleotide (SEQ ID NO:1) and partial amino acid (SEQ ID NO:2) sequences of the wild-type (WT) AHASL1D and partial nucleotide (SEQ ID NO:3) and partial amino acid (SEQ ID NO: 4) sequences of the herbicide-tolerant (HT) AHASL1D.

FIG. 1B depicts the partial nucleotide (SEQ ID NO:5) and partial amino acid (SEQ ID NO:6) sequences of the wild-type (WT) AHASL1B and partial nucleotide (SEQ ID NO:7) and partial amino acid (SEQ ID NO:8) sequences of the herbicide-tolerant (HT) AHASL1B.

FIG. 1C depicts the partial nucleotide (SEQ ID NO:9) and partial amino acid (SEQ ID NO:10) sequences of the wild-type (WT) AHASL1A and partial nucleotide (SEQ ID NO:11) and partial amino acid (SEQ ID NO:12) sequences of the herbicide-tolerant (HT) AHASL1A.

FIG. 3 is a table of percent nucleotide sequence identities from pairwise comparisons of the wheat AHASL gene coding sequences. Hexaploid IAD, Hexaploid L1B, and Hexaploid L1A denote the AHASL1D, AHASL1B, and AHASL genes, respectively, from *Triticum aestivum*. Tetraploid L1B, and Tetraploid L1A denote the AHASL1B and AHASL1A genes, respectively, from *T. turgidum* ssp. *durum*.

FIG. 7A, FIG. 7B, and FIG. 7C show is a partial alignment of the three wheat AHASL cDNA sequences (AHASL1D, SEQ ID NO:34; AHASL1B, SEQ ID NO:35; and AHASL1A, SEQ ID NO:36) with a reference position to the *Arabidopsis thaliana* AHAS nucleotide sequence.

SEQUENCE LISTING

Figure 2:
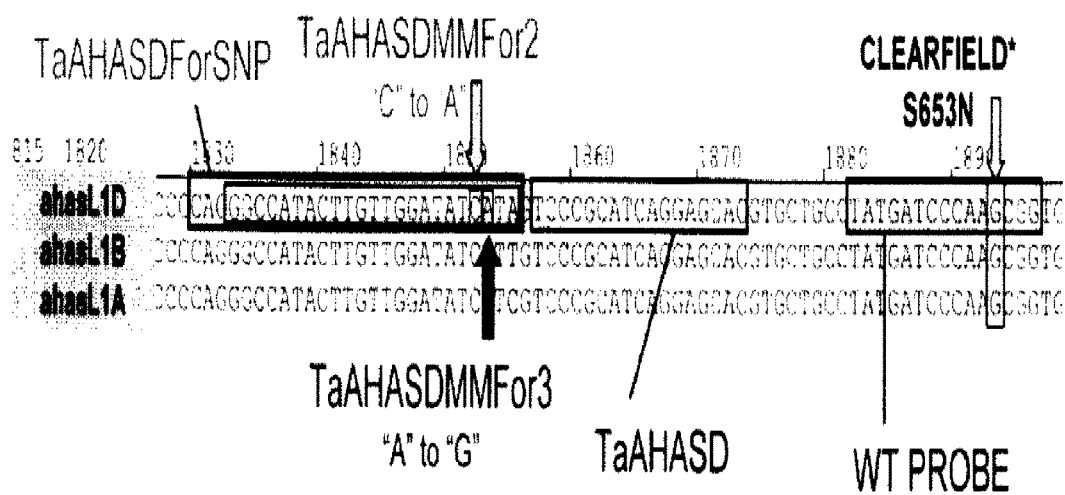
FIG. 2 depicts a partial alignment of three wheat AHASL DNA sequences (AHASL1D, AHASL1B; and AHASL1A) with AHASL forward primers TaAHASDMMFor2 (SEQ ID NO:16), TaAHASDMMFor3 (SEQ ID NO:18), TaAHASD-ForSNP (SEQ ID NO:19), and TaAHASD (SEQ ID NO:30) and a wild-type AHASL probe (SEQ ID NO:32).

The nucleic acid and amino acid sequences listed in the accompanying sequence listing are shown using standard letter abbreviations for nucleotide bases. The nucleic acid sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO:1 sets forth the nucleotide sequence of a portion of the wild-type allele of AHASL1D.

SEQ ID NO:2 sets forth the amino acid sequence encoded by the nucleotide sequence of SEQ ID NO:1.

SEQ ID NO:3 sets forth the nucleotide sequence of a portion of the herbicide-tolerant (HT) allele of AHASL1D.

SEQ ID NO:4 sets forth the amino acid sequence encoded by the nucleotide sequence of SEQ ID NO:3.

SEQ ID NO:5 sets forth the nucleotide sequence of a portion of the wild-type allele of AHASL1B.

SEQ ID NO:6 sets forth the amino acid sequence encoded by the nucleotide sequence of SEQ ID NO:5.

SEQ ID NO:7 sets forth a portion of the nucleotide sequence of the herbicide-tolerant (HT) allele of AHASL1B.

SEQ ID NO:8 sets forth the amino acid sequence encoded by the nucleotide sequence of SEQ ID NO:7.

SEQ ID NO:9 sets forth the nucleotide sequence of a portion of the wild-type allele of AHASL1A.

SEQ ID NO:10 sets forth the amino acid sequence encoded by the nucleotide sequence of SEQ ID NO:9.

SEQ ID NO:11 sets forth the nucleotide sequence of a portion of the herbicide-tolerant (HT) allele of AHASL1A.

SEQ ID NO:12 sets forth the amino acid sequence encoded by the nucleotide sequence of SEQ ID NO:11.

SEQ ID NO:13 sets forth the nucleotide sequence of an AHASL1 forward primer, which is also referred to herein as TaAHASMMFor2.

SEQ ID NO:14 sets forth the nucleotide sequence of an AHASL1 forward primer, which is also referred to herein as TaAHASMMFor3.

SEQ ID NO:15 sets forth the nucleotide sequence of a forward AHASL1D primer, which is also referred to herein as TaAHASDMMFor2Gen.

SEQ ID NO:16 sets forth the nucleotide sequence of a forward AHASL1D primer, which is also referred to herein as TaAHASDMMFor2.

SEQ ID NO:17 sets forth the nucleotide sequence of a forward AHASL1D primer, which is also referred to herein as TaAHASDMMFor3Gen.

SEQ ID NO:18 sets forth the nucleotide sequence of a forward AHASL1D primer, which is also referred to herein as TaAHASDMMFor3.

SEQ ID NO:19 sets forth the nucleotide sequence of a forward AHASL1D primer, which is also referred to herein as TaAHASDMMForSNP.

SEQ ID NO:20 sets forth the nucleotide sequence of a forward AHASL1B primer, which is also referred to herein as TaAHASBMMFor2Gen.

SEQ ID NO:21 sets forth the nucleotide sequence of a forward AHASL1B primer, which is also referred to herein as TaAHASBMMFor2.

SEQ ID NO:22 sets forth the nucleotide sequence of a forward AHASL1B primer, which is also referred to herein as TaAHASBMMFor3Gen.

SEQ ID NO:23 sets forth the nucleotide sequence of a forward AHASL1B primer, which is also referred to herein as TaAHASBMMFor3.

SEQ ID NO:24 sets forth the nucleotide sequence of a forward AHASL1B primer, which is also referred to herein as TaAHASBMMForSNP.

SEQ ID NO:25 sets forth the nucleotide sequence of a forward AHASL1A primer, which is also referred to herein as TaAHASAMMFor2Gen.

SEQ ID NO:26 sets forth the nucleotide sequence of a forward AHASL1A primer, which is also referred to herein as TaAHASAMMFor2.

SEQ ID NO: 27 sets forth the nucleotide sequence of a forward AHASL1A primer, which is also referred to herein as TaAHASAMMFor3Gen.

SEQ ID NO:28 sets forth the nucleotide sequence of a forward AHASL1A primer, which is also referred to herein as TaAHASAMMFor3.

SEQ ID NO:29 sets forth the nucleotide sequence of a forward AHASL1A primer, which is also referred to herein as TaAHASAForSNP.

SEQ ID NO:30 sets forth the nucleotide sequence of an AHASL forward primer, which is also referred to herein as TaAHASD.

SEQ ID NO:31 sets forth the nucleotide sequence of a reverse AHASL primer.

SEQ ID NO:32 sets forth the nucleotide sequence of a wild-type AHASL probe.

SEQ ID NO:33 sets forth the nucleotide sequence of a herbicide-tolerant (HT) AHASL probe.

SEQ ID NO:34 sets forth a partial wheat AHASL1D cDNA sequence.

SEQ ID NO:35 sets forth a partial wheat AHASL1B cDNA sequence.

SEQ ID NO:36 sets forth a partial wheat AHASL1A cDNA sequence.

DETAILED DESCRIPTION OF THE INVENTION

The present disclosure provides methods, kits, and primers for analyzing the genomes of plants, and particularly for analyzing the AHASL genes therein. The methods disclosed herein involve analysis of a single nucleotide polymorphism (SNP) through real-time detection of target amplification by measurement of detectable signals, for example, fluorescent signals released from reporter probes upon hybridization to SNP targets.

The methods disclosed herein involve a real-time PCR assay to determine whether a herbicide-tolerant (HT) allele or wild-type allele is present at one or more of the AHASL genes in the genome of a plant. The HT allele can comprise nucleotide sequences that encode herbicide-tolerant AHASL proteins having the S653N substitution. The methods allow for the determination of the zygosity of each AHASL gene in a plant. The methods are particularly useful for analyzing the AHASL genes of plants having multiple AHASL genes, such as, for example, bread wheat, *Triticum aestivum*, and durum wheat, *T. turgidum* ssp. *durum*.

The S653N amino acid substitution is a result of a G-to-A transition in the position that corresponds to nucleotide 1958 of the *Arabidopsis thaliana* AHASL nucleotide sequence set forth in EMBL Accession No. X51514, which is herein incorporated by reference. FIGS. 1A to 1C show the wild-type and HT nucleotide sequences and encoded amino acid sequences for AHASL1D, AHASL1B, and AHASL1A, respectively.

The methods, kits, and primers disclosed herein can be used to determine the zygosity of a plant, for example, whether a wheat plant is homozygous for the herbicide-tolerant (HT) AHASL allele, heterozygous, homozygous for the wild-type allele, hemizygous for the HT or wild-type allele, or null for the AHASL gene, in each of the three AHASL genes in a *T. aestivum* wheat plant or of the two AHASL genes in a *T. turgidum* ssp. *durum* wheat plant. The methods can be useful in breeding programs for the production of imidazolinone-tolerant wheat plants having one, two, three, four, five, or six AHASL alleles in their genomes.

*T. aestivum* has a hexaploid genome comprising three highly similar, but distinct, AHASL genes, designated as AHASL1D, AHASL1B, and AHASL1A. In contrast, *T. turgidum* ssp. *durum* has a tetraploid genome comprising two highly similar, but distinct, AHASL genes, designated as AHASL1B, and AHASL1A. While not identical, AHASL1B and AHASL1A of *T. aestivum* are closely related to AHASL1B and AHASL1A of *T. turgidum* ssp. *durum* based on sequence alignments and calculations of percentage sequence identity. FIG. 3 shows nucleotide sequence identities from pairwise comparisons of the AHASL gene coding sequences of *T. aestivum* and *T. turgidum* ssp. *durum*.

The following terms used herein are defined below.

A "primer" is a single-stranded oligonucleotide, having a 3' end and a 5' end, that is capable of annealing to an annealing site on a target DNA strand and of serving as an initiation point for DNA synthesis by a DNA polymerase, particularly in PCR amplification. Such a primer may or may not be fully complementary to its annealing site on the target DNA.

An "annealing site" on a strand of a target DNA is the site to which a primer is capable of annealing.

Generally for the amplification of a fragment of a gene by PCR, a pair of primers that anneal to opposite strands of a double-stranded DNA molecule are employed. By standard convention, the "forward primer" anneals to the non-coding strand of the gene and the "reverse primer" anneals to the coding strand.

An "AHASL forward primer" as disclosed herein and a "reverse AHASL primer" as disclosed herein are used as a primer pair in the amplification of a fragment of a particular AHASL gene, such as, for example, AHASL1D, AHASL1B, and AHASL1A of *T. aestivum* and/or AHASL1B, and AHASL1A of *T. turgidum* ssp. *durum*. An AHASL forward primer as disclosed herein can be specific to a particular AHASL gene, for example, specific to one of AHASL1D, AHASL1B, and AHASL1A. The reverse AHASL primer can be used for each AHASL gene.

The terms "herbicide-tolerant (HT) allele," "herbicide-tolerant AHASL allele," "herbicide-tolerant AHASL gene," "variant allele," "variant AHASL allele," "variant AHASL gene," "substituted allele," "substituted AHASL allele," and "substituted AHASL gene", unless indicated otherwise herein, refer to a polynucleotide that encodes an imidazolinone-tolerant AHASL protein comprising the S653N substitution.

The terms "wild-type allele," "wild-type AHASL allele," "wild-type AHASL gene," "susceptible allele," "susceptible AHASL allele," and "susceptible AHASL gene", unless indicated otherwise herein, refer to a polynucleotide that encodes an AHASL protein that lacks the S653N substitution. However, such a "wild-type allele," "wild-type AHASL allele," "wild-type AHASL gene," "susceptible allele," "susceptible AHASL allele," or "susceptible AHASL gene" can optionally comprise substitutions other than the substitution that causes the S653N substitution.

As used herein, "wild-type" or "corresponding wild-type plant" means the typical form of an organism or its genetic material, as it normally occurs, for example, as distinguished from variant, substituted, and/or recombinant forms.

Unless indicated otherwise herein, "polymerase" refers to a DNA polymerase, particularly a DNA polymerase that is suitable for use in the PCR amplifications disclosed herein, for example, Taq polymerase.

The methods disclosed herein include assays for SNP identification and zygosity determination in the AHASL genes of wheat with respect to the nucleotide transition giving the S653N substitution. The process of SNP identification as disclosed herein can be a real-time detection of target amplification by measuring fluorescent signals released from reporter molecules on the probes upon hybridization to SNP targets. This can typically be followed by enzymatic digestion of quencher molecule by Taq polymerase through PCR.

Accurate determination of a single base pair change can be extremely difficult. This is typically due to cross hybridization of the HT allele-specific and wild-type allele-specific probes to either allele regardless of actual genotype. The lack of specificity can result from the identical homology of the gene region containing the SNP of interest. The assay design can incorporate a minor groove binder or locked nucleic acid at the 3' end of the fluorescent probe to enhance the specificity.

Due to the stringent parameters associated with real-time assay development, assays are typically designed completely with the use of software. However, the assays disclosed herein can include features which are designed without the use of software or other assay-design technology, for example, primer sequences and probe sequences designed with no software or assay-design technology. In particular, AHASL forward primers disclosed herein can be designed without the use of software or other assay-design technology. In other words, the AHASL forward primers can be manually-designed. The AHASL forward primers can utilize a triallelic SNP that exists between the three AHASL genes, or a corresponding biallelic SNP that exists between two AHASL genes. Certain AHASL forward primers disclosed herein can also incorporate a deliberate nucleotide mismatch between the primer and the AHASL gene to enhance identification of the S653N substitution. Use of a deliberate nucleotide mismatch between primers and target sequences is not typical of software-designed real-time PCR assays for the AHASL gene of plants, including wheat.

As used herein, "triallelic SNP" and "biallelic SNP" refer to single nucleotide polymorphisms between different AHASL genes in a multigene plant, for example, between each of the AHASL1D, AHASL1B, and AHASL1A genes of a hexaploid wheat or between each of the AHASL1B and AHASL1A genes of a tetraploid wheat. Triallelic SNP and biallelic SNP, as used herein, can identify a particular AHASL gene of a plant having multiple AHASL genes. Triallelic SNP and biallelic SNP, as used herein, do not distinguish between wild-type and HT AHASL alleles.

AHASL forward primers used in the methods disclosed herein are referred to as TaAHASMMFor2 (SEQ ID NO:13) and TaAHASMMFor3 (SEQ ID NO:14). The methods disclosed herein can use AHASL forward primers which can be specific for a particular AHASL gene. AHASL1D forward primers for use in the methods disclosed herein are referred to as TaAHASDMMFor2Gen primer (SEQ ID NO:15), TaAHASDMMFor2 primer (SEQ ID NO:16), TaAHASDMMFor3Gen primer (SEQ ID NO:17), TaAHASDMMFor3 primer (SEQ ID NO:18), and TaAHASDForSNP primer (SEQ ID NO:19). AHASL1B forward primers for use in the methods disclosed herein are referred to as TaAHASBMMFor2Gen primer (SEQ ID NO:20), TaAHAS-BMMFor2 primer (SEQ ID NO:21), TaAHASBMMFor3Gen primer (SEQ ID NO:22), TaAHAS-BMMFor3 primer (SEQ ID NO:23), and TaAHASBForSNP primer (SEQ ID NO:24). AHASL1A forward primers for use in the methods disclosed herein are referred to as TaAHASAMMFor2Gen primer (SEQ ID NO:25), TaAHASAMMFor2 primer (SEQ ID NO:26), TaAHASAMMFor3Gen primer (SEQ ID NO:27), TaAHASAMMFor3 primer (SEQ ID NO:28), and TaAHASAForSNP primer (SEQ ID NO:29). The AHASLB and AHASLA forward primers are suitable for use in *T. aestivum* and *T. turgidum* ssp. *durum*.

These AHASL forward primers are designed without the use of software or other assay-design technology and incorporate a triallelic SNP between the AHASL1D, AHASL1A, and AHASL1B genomes of *T. aestivum*, or, in the case of *T. turgidum* ssp. *durum*, a biallelic SNP between AHAS1A and AHASL1B. The SNP is positioned approximately 40 nucleotides upstream from the substitution encoding the S653N substitution. The SNP for each genome of *T. aestivum* is as follows: AHASL1D has an adenine, AHASL1B has a thymine, and AHASL1A has a cytosine. The SNPs for AHASL1B and AHASL1A are the same in *T. turgidum* ssp. *durum*.

In addition to incorporation of the triallelic SNP in the AHASL forward primer design, the TaAHASMMFor2 (SEQ ID NO:13), TaAHASMMFor3 (SEQ ID NO:14), TaAHASDMMFor2Gen (SEQ ID NO:15), TaAHASDM-MFor2 (SEQ ID NO:16), TaAHASBMMFor2Gen (SEQ ID NO:20), TaAHASBMMFor2 (SEQ ID NO:21), TaAHASBMMFor3Gen (SEQ ID NO:22), TaAHASBM-MFor3 (SEQ ID NO:23), TaAHASAMMFor2Gen (SEQ ID NO: 25), TaAHASAMMFor2 (SEQ ID NO:26), TaAHASAMMFor3Gen (SEQ ID NO:27), and TaAHASM-MFor3 (SEQ ID NO:28) forward primers have a deliberate nucleotide mismatch with the AHASL gene located three nucleotides upstream from the terminal nucleotide of the primer. The deliberate nucleotide mismatch of the TaAH-ASDMMFor2 (SEQ ID NO:16) forward primer is shown in FIG. 2. FIG. 2 depicts the mismatched nucleotide as a C-to-A mismatch located 3 nucleotides upstream of the 3'-terminal nucleotide. The TaAHASBMMFor2 (SEQ ID NO:21), TaAHASAMMFor2 (SEQ ID NO:26), and TaAHASAMMFor3 (SEQ ID NO:28) primers also can have the C-to-A deliberate mismatch. The TaAHASBMMFor3 (SEQ ID NO:23) primer can have a C-to-G deliberate mismatch. The mismatch can be a C-to-A mismatch, a C-to-G mismatch or a C-to-T mismatch, as in the TaAHASMMFor2 (SEQ ID NO:13), TaAHASMMFor3 (SEQ ID NO:14), TaAHASDMMFor2Gen (SEQ ID NO:15), TaAHASBMMFor2Gen (SEQ ID NO:20), TaAHASBMMFor3Gen (SEQ ID NO:22), TaAHASAMMFor2Gen (SEQ ID NO: 23), and TaAHASAMMFor3Gen (SEQ ID NO:27) primers.

In addition to incorporation of the triallelic SNP in the AHASL forward primer design, the TaAHASDMMFor3Gen (SEQ ID NO:17) and TaAHASDMMFor3 (SEQ ID NO:18) forward primers have a deliberate nucleotide mismatch with the AHASL gene located two nucleotides upstream from the terminal nucleotide of the primer. The deliberate nucleotide mismatch of the TaAHASDMMFor3 (SEQ ID NO:18) primer is shown in FIG. 2. FIG. 2 depicts the mismatched nucleotide as an A-to-G mismatch. However, the mismatch can be an A-to-G mismatch, an A-to-C mismatch or an A-to-T mismatch, as in the TaAHASDMMFor3Gen (SEQ ID NO:17) primer.

Use of the deliberate nucleotide mismatch between the AHASL forward primer and AHASL gene can improve the accuracy of zygosity calls in real-time assays as compared to AHASL forward primers incorporating the triallelic SNP but not having an additional mismatched nucleotide. For example, the TaAHASDForSNP primer does not include the deliberately mismatched nucleotide as in the TaAHASDM-MFor2 and TaAHASDMMFor3 primers. The TaAHASD-ForSNP primer does not provide zygosity calls in a real-time PCR assay as accurately as the TaAHASDMMFor2 and TaAHASDMMFor3 primers.

The AHASL forward primers incorporating the triallelic SNP of the AHASL gene can have a melting temperature $T_m$ outside of the recommended melting temperature range for real-time PCR based techniques. The recommended melting temperature range for primers used in real-time PCR based techniques can be in the range of 58-60° C. The melting temperature of the AHASL forward primers disclosed herein can be around 54° C.

The above-described AHASL forward primers are not limited to oligonucleotides of the exact length of the sequences given in SEQ ID NO:13 to SEQ ID NO:29. The AHASL forward primers used in the methods disclosed herein can be shorter in length so long as they include the triallelic or biallelic SNP as the terminal nucleotide and, optionally, the above-described deliberate mismatch. For example, suitable AHASL forward primers can comprise the ten to fifteen terminal nucleotides given in SEQ ID NO:13 to SEQ ID NO:29.

The TaAHASD forward primer (SEQ ID NO:30) is a computer-designed primer. This computer-designed primer does not include the triallelic SNP between the AHASL genes or a deliberate nucleotide mismatch between primer and target as incorporated in the manually designed AHASL forward primers. Although designed as a forward primer for the AHASL1D gene, the TaAHASD forward primer can be used in the AHASL1B and AHASL1A genes. However, the TaAHASD forward primer is unsuitable for use in a real-time PCR assay to analyze AHASL genes as it fails to distinguish between homozygous wild-type and heterozygous.

As noted, the TaAHASMMFor2, TaAHASMMFor3, TaAHASDMMFor2Gen, TaAHASDMMFor2, TaAHASDMMFor3Gen, TaAHASDMMFor3, TaAHASD-ForSNP, TaAHASBMMFor2Gen, TaAHASBMMFor2, TaAHASBMMFor3Gen, TaAHASBMMFor3, TaAHASB-ForSNP, TaAHASAMMFor2Gen, TaAHASAMMFor2, TaAHASAMMFor3Gen, TaAHASAMMFor2, and TaAHASAForSNP primers are designed without the use of software or other assay-design technology. Primer design software rejects these primer designs as being unsuitable for a real-time PCR assay to analyze plant AHASL genes.

A reverse AHASL primer for use in the methods disclosed herein is given by SEQ ID NO:31. The reverse AHASL primer can be used for the AHASL1D, AHASL1B, and AHASL1A genes. The reverse AHASL primer aligns with the AHASL gene downstream from the nucleotide substitution which results in the S653N substitution.

Reverse AHASL primers suitable for the methods disclosed herein are not limited to oligonucleotides having the sequence as set forth in SEQ ID NO:31. Suitable reverse AHASL primers can be selected to produce an amplicon having a maximum length of 200 base pairs, of which the forward primer and probe occupy from 40 to 80 base pairs of the amplicon, preferably, 50 to 75 base pairs, more preferably, 60 to 75 based pairs, and most preferably, about 67 base pairs. The amplicon can be about 100-200 base pairs in length, preferably about 120-180 base pairs, more preferably about 140-160 base pairs, and most preferably about 150 to about 160 base pairs in length. The amplicon can be about 155 base pairs or about 156 base pairs in length. An amplicon that is longer than 200 base pairs can result in non-specific amplification of genomic DNA. Suitable reverse AHASL primers can have a melting temperature in the range of about 55° C. to about 60° C.

For SNP analysis, two oligonucleotide probes are designed to differentiate the two different alleles: wild-type/susceptible and variant/herbicide-tolerant. A suitable wild-type probe is given by SEQ ID NO:32. A suitable herbicide-tolerant (HT) probe is given by SEQ ID NO:33. Each probe has a different detectable signal, for example, different fluorescent molecules, which can be independently detected within a duplex PCR, for example, by emitting fluorescent signals of differing wavelengths. Suitable probes for use in the methods disclosed herein are not limited to probes given by SEQ ID NO:32 and SEQ ID NO:33. For example, suitable probes can differ in length from the probes of SEQ ID NO:32 and SEQ ID NO:33. As a further example, suitable probes can be designed to anneal to either strand, e.g., a reverse probe.

The HT probe is designed to hybridize specifically to the resistant allele and the wild-type probe is specific to the susceptible allele. In the methods disclosed herein, both the HT and wild-type probes can be mixed in the same well with a common set of PCR primers, for example, one of the forward AHASL primers and the reverse AHASL primer. Each of the HT and wild-type probes hybridizes specifically to the AHASL region carrying the SNP located between the forward and reverse primers. Both probes align and hybridize with the region of the AHASL genes containing the single nucleotide polymorphism resulting in the S653N substitution. 5' exonuclease activity during polymerase extension of a probe with a perfect match will result in cleavage of the reporter molecule emitting a fluorescent signal. Wavelengths of fluorescent signal are measured by a real-time thermocycler.

The difference in the accumulation of fluorescent signals between the HT and wild-type alleles are calculated at a specific point during the amplification referred to as the "cycle at threshold value" or "Ct value". The threshold can be determined manually or automatically by the software associated with the real-time instrumentation. The threshold is typically set to allow signal measurement during the exponential phase of the PCR. These thermal cycle threshold values, from both wavelengths, are then compared and genotypes are determined.

In a real-time PCR assay, zygosity calls and genotype designations can be calculated by subtracting the Ct value of the wild-type probe from the Ct value of the HT probe. This calculation provides a "delta Ct value", also referred to as a "dCt value" for each sample. Delta Ct values of the wild-type, heterozygous, and homozygous herbicide-tolerant standard controls can be used to provide a benchmark for determining zygosity calls of unknown samples. The dCt values for homozygous HT and heterozygous samples can be a negative number. The values of standard controls can be used to segregate the genotype clusters of the unknown samples. Therefore, it is critical to include standard controls from known genotypes on every PCR plate. Graphing the dCt values in a scatter plot can assist interpretation of the results.

Cutoff values to determine zygosity are obtained from the control samples by automatically calculating the average between the duplicate dCts for the relevant range. The cutoff values are established to distinguish between homozygous wild-type and heterozygous, and between heterozygous and homozygous herbicide-tolerant. Assays for different AHASL genes, e.g., AHASL1D, AHASL1B, or AHASL1A, can have a different range of delta Ct values for the control set. The range is dependent upon primer efficiencies, which can be reduced due to a limited region of interest for SNP detection; SNP probe specificity, and inherent variability that occurs between plates.

The methods described herein are not limited to a particular fluorophore and quencher molecule. The selection of a particular fluorophore can depend on the type of assay platform used and acceptable fluorophores for a device are typically provided in manufacturers' instructions. For the methods described herein, reporter molecules can have a fluorescence emission range from 500-660 nm. Fluorophores with this emission range include FAM, TET, JOE, Yakima Yellow, VIC, Hex, Cy3, TAMRA, Texas Red, and Redmond Red. Cy5 has a fluorescence emission outside of the 500-660 nm range, but can be used. BHQ-1 and BHQ-plus-1 can be used as quencher molecules. Selection of a particular quencher molecule can be based on the fluorophore selection and the probe length as understood by one of ordinary skill in the art.

Although the methods disclosed herein have been described in analyzing the AHASL genes of hexaploid and tetraploid wheat plants, the methods can be used in analyzing the AHASL genes of diploid wheat plants, for example, einkorn wheat (*Trificum monococcum*). For example, the forward AHASL1A primers, TaAHASAMMFor2Gen (SEQ ID NO:25), TaAHASAMMFor2 (SEQ ID NO:26), TaAHASAMMFor3Gen (SEQ ID NO:27), TaAHASMMFor3 (SEQ ID NO:28), and TaAHASAForSNP (SEQ ID NO:29) are suitable for use in a real-time PCR assay to determine the zygosity of the AHASL gene in einkorn wheat. Such methods can also make use of the reverse AHASL primer, wild-type AHASL probes, and HT AHASL probes described herein.

The methods disclosed herein can be adapted for multiplex designs to analyze and to determine the zygosity of plant AHASL genes, including real-time multiplex PCR assays. For example, probes can be designed to incorporate, as the 5' end nucleotide thereof, a triallelic SNP nucleotide and, as the 3' end nucleotide, the nucleotide at the position of the G-to-A substitution that gives rise to the S653N substitution. Suitable probes for use in multiplex designs can range in length from about 15 nucleotides to about 250 nucleotides, preferably from about 25 nucleotides to about 50 nucleotides. Probe length can optimized according to the type of assay platform as understood by one of ordinary skill in the art. For example, the methods and primers disclosed herein can be adapted for use in Invader®-based assay platforms, molecular beacon assay platforms, Luminex®-based assay platforms, Scorpion®-based assay platforms, TaqMan®-based assay platforms, and Amplifluor®-based assay platforms These assay platforms can make use of probes having lengths of 50-150 nucleotides, 80-140 nucleotides, 100-130 nucleotides, or 120 nucleotides. Probes can also be designed in hairpin-loop conformations, such as a molecular beacon.

In a real-time multiplex PCR assay, probes can be labeled as understood by a person of ordinary skill in the art. For example, sets of probes can be designed making use of two or three different fluorophores, one for each allele-specific SNP for distinguishing between the genomic alleles of polyploid wheat. A fluorophore for identifying wild-type alleles and a fluorophore for identifying herbicide-tolerant alleles can be used. This can provide for allele specific detection and, when used with the above-described AHASL forward primers, allele specific amplification. Such probes can be used, for example, in a multiplex assay using the above-described AHASL forward primers or a universal set of AHASL forward primers.

The present disclosure also provides kits for performing the methods described herein. Such kits can comprise at least one AHASL forward primer described herein, at least one AHASL reverse primer, at least one polymerase capable of catalyzing the PCR amplification, at least one HT-allele probe, and at least one wild-type allele probe, wherein the probes include a reporter molecule.

The present disclosure also provides AHASL forward primers as described herein.

The forward primers described herein can be used in assay formats which do not use probes, for example, agarose gel assays and pyrosequencing assays. Such methods can include steps of providing DNA comprising the plant AHASL genes; amplifying the DNA using an AHASL forward primer, an AHASL reverse primer, polymerase, and deoxyribonucleotide triphosphates; and detecting products of the amplification thereby identifying the zygosity of the AHASL gene; wherein the AHASL forward primer is an oligonucleotide having a sequence comprising the ten terminal nucleotides of SEQ ID NO:13, SEQ ID NO:14, or SEQ ID NO:17. For these methods, detecting products of the amplification can involve techniques suitable for such assay platforms as understood by one of ordinary skill in the art.

While the methods and kits disclosed herein do not depend on PCR primers of any particularly number of nucleotides, it is recognized that the portion of a PCR primer that anneals to its complementary target on the template DNA will generally be between about 10 and 50 contiguous nucleotides, preferably 10, 11, 12, 13, 14, 15, 16, 17, 18, 19, 20, 21, 22, 23, 24, 25, 26, 27, 28, 29, 30, or more contiguous nucleotides. However, a PCR primer of the invention can further comprise on its 5' end additional nucleotides that are not intended to anneal to the target such as, for example, a DNA sequence comprising one or more restriction enzyme recognition sites, short tandem repeats, variable number of tandem repeats, simple sequence repeats, and simple sequence length polymorphisms.

The methods disclosed herein involve the use of DNA polymerases for PCR amplification of DNA. The methods do not depend on a particular DNA polymerase for PCR amplification of DNA, only that such polymerases are capable of amplifying one or more of the plant AHASL genes or fragments thereof and comprises a 5'-3' exonuclease activity, including but not limited to: Taq polymerases; Pfu polymerases; Tth polymerases; Tfl polymerases; Tfu polymerases; thermostable DNA polymerases from *Thermococcus gorgonarious* which are also known as Tgo DNA polymerases; thermostable DNA polymerases from *Thermococcus litoralis* such as, for example, those that are known as Vent® DNA polymerases, thermostable DNA polymerases from *Pyrococcus* species GB-D such as, for example, those that are known as Deep Vent® DNA polymerases; and modified versions and mixtures thereof. Preferably, the DNA polymerases used in the disclosed methods are thermostable DNA polymerases, DNA polymerases having 5' to 3' exonuclease activity, and/or DNA polymerases having proofreading activity.

The methods disclosed herein involve the amplification of a target DNA sequence by PCR. In certain embodiments, the target DNA sequence can be amplified directly from a sample comprising genomic DNA isolated from at least one plant or part, organ, tissue, or cell thereof. Those of ordinary skill in the art will recognize that the amount or concentration of genomic DNA will depend on any number of factors including, but not limited to, the PCR conditions (e.g., annealing temperature, denaturation temperature, the number of cycles, primer concentrations, dNTP concentrations, and the like), the thermostable DNA polymerase, the sequence of the primers, and the sequence of the target. Typically, in the embodiments described herein, the concentration of genomic DNA is at least or about 5 ng/µL to about 100 ng/µL.

The methods disclosed herein are also suitable for use with DNA other than genomic DNA. For example, cDNA or gene specific PCR products can be used as initial DNA templates in the methods disclosed herein.

In addition to PCR amplification, the methods disclosed herein can involve various techniques of molecular biology including, for example, DNA isolation, genomic DNA isolation, digestion of DNA by restriction enzymes and nucleases, DNA ligation, DNA sequencing, and the like.

The methods disclosed herein involve the use of genomic DNA isolated from a plant. The methods of the invention do not depend on genomic DNA isolated by any particular method. Any method known in the art for isolating, or purifying, from a plant, genomic DNA, which can be used a source of template DNA for the PCR amplifications described above, can be employed in the methods of the invention. Preferably, such methods for isolating plant genomic DNA are suited, or can be adapted by one of ordinary skill in the art, for the isolation of genomic DNA from relatively large numbers of tissue samples of plants.

For the methods disclosed herein, genomic DNA can be isolated from whole plants or any part, organ, tissue, or cell thereof. For example, genomic DNA can be isolated from seedlings, leaves, stems, roots, inflorescences, seeds, embryos, tillers, coleoptiles, anthers, stigmas, cultured cells, and the like. Furthermore, the methods do not depend on the isolation of genomic DNA from plants or parts, organs, tissues, or cells thereof that are of any particular developmental stage. The methods can employ genomic DNA that is isolated from, for example, seedlings or mature plants, or any part, organ, tissue or cell thereof. Furthermore, the methods do not depend on plants that are grown under any particular conditions. The plants can be grown, for example, under field conditions, in a greenhouse, or a growth chamber, in culture, or even hydroponically in a greenhouse or growth chamber. Typically, the plants will be grown in conditions of light, temperature, nutrients, and moisture that favor the growth and development of the plants. Additionally, for methods disclosed herein, genomic DNA can be isolated from agronomic products, for example, seed oil, seed meal, and the like.

It will be readily apparent to one of ordinary skill in the relevant arts that other suitable modifications and adaptations to the methods and applications described herein are obvious and can be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Specific examples of the methods disclosed herein are provided below.

Example 1

AHASL Genes of Wheat

For *Triticum aestivum*, three acetohydroxyacid synthase large subunit (AHASL) sequence variants are identified from sequencing of wheat cDNAs. The genes corresponding to these variants are mapped to their respective genome and chromosome arm (6 L) and are named on the basis of the genome in which they reside (e.g., AHASL on genome A=AHASL1A). Nucleotide sequences for multiple varieties of *Triticum aestivum* AHASL1A, AHASL1B and AHASL1D transcripts are obtained. These sequences comprise the full coding sequences for the mature polypeptides.

For *T. turgidum* ssp. *durum*, two acetohydroxyacid synthase large subunit (AHASL) sequence variants are identified from sequencing of wheat cDNAs. The genes corresponding to these variants are mapped to their respective genome and are named on the basis of the genome in which they reside (e.g., AHASL on genome A=AHASL1A). Nucleotide sequences for multiple varieties of *T. turgidum* ssp. *durum* AHASL1A and AHASL1B transcripts are obtained. These sequences comprise the full coding sequences for the mature polypeptides.

For *Triticum aestivum* and *T. turgidum* ssp. *durum*, a comparison of imidazolinone (IMI)-tolerant varieties with wild-type progenitors shows that the most common type of substitution is a G-to-A transition, which produces a serine (S) to asparagine (N) substitution in a position corresponding to 5653 in the model taxon, *Arabidopsis thaliana*.

A comparison of the AHASL sequences of the A, B, and D genomes of *Triticum aestivum* (i.e., AHASL1A, AHASL1B and AHASL1D) shows that there is a triallelic SNP located approximately 40 nucleotides upstream from the transition producing the S653N substitution. The polymorphism at this position is an adenine on the D genome, a thymine on the B genome, and a cytosine on the A genome.

A comparison of the AHASL sequences of the A and B genomes of *T. turgidum* ssp. *durum* (i.e., AHASL1A and AHASL1B) shows that there is a biallelic SNP located approximately 40 nucleotides upstream from the transition producing the S653N substitution. The polymorphism at this position is a thymine on the B genome, and a cytosine on the A genome.

Example 2

Forward Primer Design

Forward primers are designed for use in an assay, for example, a real-time PCR assay, for detection of the S653N substitution in wheat. The TaAHASD primer (SEQ ID NO:30) is a software-designed primer (i.e., a forward primer designed by the assay design program RealTimeDesign by BioSearch Technologies.)

Additional forward primers are designed without the use of software or assay-design technology based on the SNP between AHASL genomes described in Example 1. These primers incorporate the SNP as the terminal nucleotide of the primer. Certain forward primers are designed to include a deliberate nucleotide mismatch with the target nucleotide sequence located 2 or 3 nucleotides upstream from the terminal nucleotide of the primer. Each primer can be specific for an AHASL gene on a particular genome. Each forward primer for the AHASL B genome and A genome can be used in *Triticum aestivum* and *T. turgidum* ssp. *durum*.

The manually-designed forward primers for the AHASL1D genome are designated as TaAHASDMMFor2 primer (SEQ ID NO:16), TaAHASDMMFor3 primer (SEQ ID NO:18), and TaAHASDForSNP primer (SEQ ID NO:19). The manually-designed forward primers for the AHASL1B genome are designated as TaAHASBMMFor2 primer (SEQ ID NO:21), TaAHASBMMFor3 primer (SEQ ID NO:23), and TaAHASBForSNP primer (SEQ ID NO:24). The manually-designed primers for the AHASL1A genome are designated as TaAHASAMMFor2 primer (SEQ ID NO:26), TaAHASAMMFor3 primer (2SEQ ID NO:28), and TaAHASAForSNP primer (SEQ ID NO:29). The melting temperature $T_m$ of the primers incorporating the triallelic SNP is about 54° C.

The TaAHASDMMFor2 primer (SEQ ID NO:16), TaAHASBMMFor2 primer (SEQ ID NO:21), TaAHASAMMFor2 primer (SEQ ID NO:26), and TaAHASAMMFor3 primer (SEQ ID NO: 28) have a deliberate nucleotide mismatch three nucleotides upstream from the terminal nucleotide of the primer. The mismatch is a C-to-A substitution from the AHASL nucleotide sequence.

The TaAHASBMMFor3 primer (SEQ ID NO:23) has a deliberate nucleotide mismatch three nucleotides upstream from the terminal nucleotide of the primer. The mismatch is a C-to-G substitution from the AHASL nucleotide sequence.

The TaAHASDMMFor3 primer (SEQ ID NO:18) has a deliberate nucleotide mismatch two nucleotides upstream from the terminal nucleotide of the primer. The mismatch is an A-to-G substitution from the AHASL nucleotide sequence.

The primer design program RealTimeDesign rejects the above-described manually designed forward primers for use in real-time PCR assay designs. The default parameters are the "most restrictive" parameters. The program still rejects the manually designed forward primers under the "least restrictive" primer design parameters.

The primer design program RealTimeDesign provides the sequence for the forward AHASL primer TaAHASD (SEQ ID NO:30).

Example 3

Validation of AHASL Forward Primers

Real-time assays using wheat AHASL samples of known zygosity are conducted with the TaAHASDMMFor2 primer (SEQ ID NO:16), TaAHASDMMFor3 primer (SEQ ID NO:18), TaAHASDForSNP primer (SEQ ID NO:19), TaAHASBMMFor2 primer (SEQ ID NO:21), TaAHASBMMFor3 primer (SEQ ID NO:23), TaAHASBForSNP primer (SEQ ID NO:24), TaAHASAMMFor2 primer (SEQ ID NO:26), TaAHASAMMFor3 primer (SEQ ID NO:28), TaAHASAForSNP primer (SEQ ID NO:29), and TaAHASD primer (SEQ ID NO:30) for validation purposes.

Samples can be obtained by extracting genomic DNA from bulk flour of wheat varieties representing, for example, S653N homozygous variants of the AHASL1D, AHASL1B, and AHASL1A genes of *T. aestivum* and AHASL1B and AHASL1A genes of *T. turgidum* ssp. *durum*. A heterozygous sample can be produced, for example, for control purposes, by combining genomic DNA of a wheat plant having a wild-type AHASL gene (identified as "Group W" herein) and a homozygous variant for the AHASL1D gene (identified as "Group D" and "CV9804" herein) in a 1:1 ratio. The genomic DNA is subdivided into aliquots of three replicates for each variety.

A solution for each forward primer is prepared to provide 25× concentrated mixes (referred to herein as "WheatD-SNP") as shown in Table 1. The reverse AHASL primer (SEQ ID NO:31), AHASL wild-type probe (SEQ ID NO:32), and AHASL HT probe (SEQ ID NO:33) are included in each of the stock solutions. Each of the WheatD-SNP mixes is stored at −20° C.

TABLE 1

| WheatDSNP mix | Reagent | Final Conc. (μM) |
|---|---|---|
| 100 μl 25x Stock: | 22.5 μl 100 μM Forward Primer | 22.5 |
| | 22.5 μl 100 μM Reverse Primer | 22.5 |
| | 5 μl 100 μM Probe (Wildtype) | 5 |
| | 5 μl 100 μM Probe (HT) | 5 |
| | 45 μl ddH$_2$O | N/A |

A polymerase mix ("Supplemented 2× Polymerase Mix") is prepared as shown in Table 2. The Supplemented 2× Polymerase Mix is stored at 4° C.

TABLE 2

| Supplement the entire 10 ml stock solution upon receipt at first thawing. | Final Conc. (2x) |
|---|---|
| 10 ml 2x Polymerase Mix | Contains 3 mM MgCl$_2$ |
| 110 μl 1M MgCl$_2$ | 11 mM |
| 40 μl 300 uM Sulforhodamine 101 (Sigma Catalog #S7635) | 1200 nM |

A master mix for the real-time assay for the AHASL1D Sb53N is prepared from each of the Wheat DSNP mixes and Supplemented 2× Polymerase Mix as shown in Table 3.

TABLE 3

| 1x Master Mix Components | x μl per 5 μl rxn | Vol. in μl per 96-Well Plate (130 rxns) | Final Conc. |
|---|---|---|---|
| Supplemented 2x Polymerase Miix | 2.5 | 325 | 1x |
| WheatDSNP 25X mix | 0.2 | 26 | 900 nM primer/ 200 nM probe |
| water | 0.3 | 39 | N/A |
| Total | 3.0 | 390 | N/A |

The real-time assay is conducted using a Biomek FxP according to the following protocol. 45 μl of 1× master mix is dispensed into each well of a strip of 8 tubes. The strip is placed on a designated 96 well plate rack with column 1 for quadrant 1, column 2 for quadrant 2, column 3 for quadrant 3, and column 4 for quadrant 4 of a 384 well PCR reaction plate. 3 μl of 'WheatDSNP' Real-time working master mix (1×) per well 2 μl DNA eluted in 1×TE per well (gDNA starting concentration is approximately 5-10 ng/μl). The plates are immediately sealed with optical sealing tape and are run for 2 minutes at 1000 rpm. The plates can be stored at 4° C. for up to 48 hours.

The plate is run on the light cycler under the cycling conditions show in Table 4.

TABLE 4

| Reaction Condition | Temp ° C. | Time | Repeat |
|---|---|---|---|
| Cycle | 95 | 5:00 | 0 |
| Hold | 95 | 0:20 | 40 |
| Cycle | 60 | 1:00 | |

Total runtime ~1:40

From the results of the real-time PCR assay, zygosity call and genotype designations are made by subtracting the Ct (cycle at threshold) value of the wildtype specific probe from the Ct value of the HT specific probe to obtain a delta Ct (dCt) value for each control sample. The dCt value of the homozygous wild-type, heterozygous, and homozygous HT standard controls provide the benchmark for determining zygosity calls of unknown samples. The values of the standard controls can be used to segregate the genotype clusters of unknown samples. Graphing the dCt values in a scatter plot can assist interpretation of the results.

The cutoff values are obtained from the control samples by automatically calculating the average between the duplicate dCts for the relevant range. There is a cutoff generated between null (homozygous wild-type) and heterozygous, and a cutoff generated between heterozygous and homozygous variant. The sample genotype calls are made based on these cutoff values.

Figure 4:
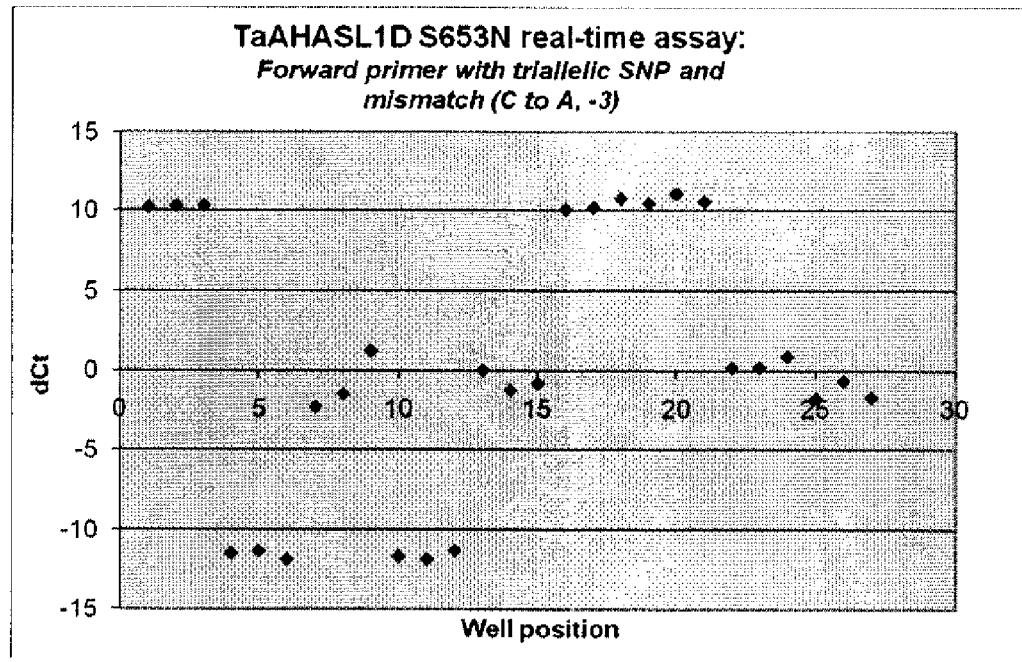
FIG. 4 is a scatter plot of dCt values of a validation assay using the TaAHASDMMFor2 primer (SEQ ID NO:16).

Table 5 and its Legend provide validation data for the TaAHASDMMFor2 (SEQ ID NO:16) forward primer. FIG. 4 shows a scatter plot of the dCt values from the data.

TABLE 5

| Sample | Assay | Sample ID | HT Ct | Wildtype Ct | dCt | Zygosity Call (dCt Method) | Comments |
|---|---|---|---|---|---|---|---|
| A1 | 26 | Wildtype | 40 | 40 | ND | No DNA | |
| B1 | 74 | Wildtype | 40 | 40 | ND | No DNA | |
| C1 | 122 | Heterozygous | 40 | 40 | ND | No DNA | |
| D1 | 170 | Heterozygous | 40 | 40 | ND | No DNA | |
| E1 | 218 | Homozygous | 40 | 40 | ND | No DNA | |
| F1 | 266 | Homozygous | 40 | 40 | ND | No DNA | |
| G1 | 314 | | | | | | |
| H1 | 362 | | | | | | |
| A2 | 28 | Group W | 40 | 29.803118 | 10.196882 | Wildtype | Wildtype bread wheat |
| B2 | 76 | Group W | 40 | 29.724152 | 10.275848 | Wildtype | Wildtype bread wheat |
| C2 | 124 | Group W | 40 | 29.708704 | 10.291296 | Wildtype | Wildtype bread wheat |
| D2 | 172 | Group D | 28.533606 | 40 | −11.466394 | Homozygous | D HTbread wheat |
| E2 | 220 | Group D | 28.649118 | 40 | −11.350882 | Homozygous | D HT bread wheat |
| F2 | 268 | Group D | 28.12679 | 40 | −11.87321 | Homozygous | D HT bread wheat |
| G2 | 316 | Group D HET | 29.184525 | 31.502728 | −2.318203 | Heterozygous | D het bread wheat |
| H2 | 364 | Group D HET | 29.702597 | 31.20019 | −1.497593 | Heterozygous | D het bread wheat |
| A3 | 30 | Group D HET | 30.94369 | 29.723372 | 1.220318 | Heterozygous | D het bread wheat |
| B3 | 78 | CV9804 | 28.315844 | 40 | −11.684156 | Homozygous | D HT bread wheat |
| C3 | 126 | CV9804 | 28.134075 | 40 | −11.865925 | Homozygous | D HTbread wheat |
| D3 | 174 | CV9804 | 28.69106 | 40 | −11.30894 | Homozygous | D HT bread wheat |
| E3 | 222 | CV9804 HET | 30.412355 | 30.413248 | −0.000893 | Heterozygous | D het bread wheat |
| F3 | 270 | CV9804 HET | 29.99291 | 31.235846 | −1.242936 | Heterozygous | D het bread wheat |
| G3 | 318 | CV9804 HET | 30.114641 | 30.941849 | −0.827208 | Heterozygous | D het bread wheat |

TABLE 5-continued

| | | | | | | | |
|---|---|---|---|---|---|---|---|
| H3 | 366 | BW255-2 | 40 | 29.943615 | 10.056385 | Wildtype | A HT bread wheat |
| A4 | 32 | BW255-2 | 40 | 29.805761 | 10.194239 | Wildtype | A HT bread wheat |
| B4 | 80 | BW255-2 | 40 | 29.25382 | 10.74618 | Wildtype | A HT bread wheat |
| C4 | 128 | Group B | 40 | 29.5461 | 10.4539 | Wildtype | B HT bread wheat |
| D4 | 176 | Group B | 40 | 28.947887 | 11.052113 | Wildtype | B HT bread wheat |
| E4 | 224 | Group B | 40 | 29.434076 | 10.565924 | Wildtype | B HT bread wheat |
| F4 | 272 | UT-12-2 | 36.31313 | 36.140057 | 0.173073 | No DNA | Durum wheat |
| G4 | 320 | UT-12-2 | 35.846695 | 35.667755 | 0.17894 | No DNA | Durum wheat |
| H4 | 368 | UT-12-2 | 37.536434 | 36.63924 | 0.897194 | No DNA | Durum wheat |
| A5 | 34 | DIMI-39 | 35.83397 | 37.589897 | −1.755927 | No DNA | Durum wheat |
| B5 | 82 | DIMI-39 | 36.14197 | 36.788425 | −0.646455 | No DNA | Durum wheat |
| C5 | 130 | DIMI-39 | 35.096363 | 36.812702 | −1.716339 | No DNA | Durum wheat |

LEGEND
dCt Cutoff between Null and Het   5
dCt Cutoff between Het and Homo  −5
WT-TET Cutoff                    39
HT-FAM Cutoff                    39

Figure 5:
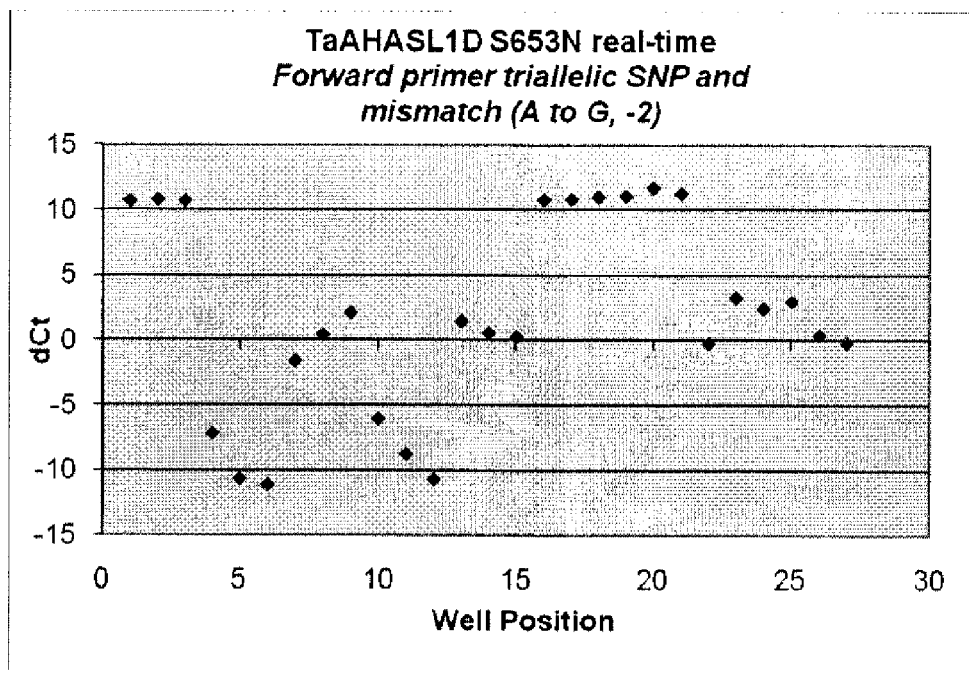
FIG. 5 is a scatter plot of dCt values of a validation assay using the TaAHASDMMFor3 primer (SEQ ID NO:18).

Table 6 and its Legend provide validation data for the TaAHASDMMFor3 (SEQ ID NO:18) forward primer. FIG. 5 shows a scatter plot of the dCt values from the data. replicates and increases separation in dCt values between homozygous wild-type, heterozygous, and homozygous herbicide-tolerant samples over the TaAHASDMMFor3 for-

TABLE 6

| Sample | Assay | Sample ID | HT Ct | Wildtype Ct | dCt | Zygosity Call (dCt Method) |
|---|---|---|---|---|---|---|
| A1 | 25 | Wildtype | 40 | 40 | ND | No DNA |
| B1 | 73 | Wildtype | 40 | 40 | ND | No DNA |
| C1 | 121 | Heterozygous | 40 | 40 | ND | No DNA |
| D1 | 169 | Heterozygous | 40 | 40 | ND | No DNA |
| E1 | 217 | Homozygous | 40 | 40 | ND | No DNA |
| F1 | 265 | Homozygous | 40 | 40 | ND | No DNA |
| G1 | 313 | | | | | |
| H1 | 361 | | | | | |
| A2 | 27 | Group W | 40 | 29.34243 | 10.65757 | Wildtype |
| B2 | 75 | Group W | 40 | 29.224567 | 10.775433 | Wildtype |
| C2 | 123 | Group W | 40 | 29.310955 | 10.689045 | Wildtype |
| D2 | 171 | Group D | 29.380377 | 36.519726 | −7.139349 | Homozygous |
| E2 | 219 | Group D | 29.383379 | 40 | −10.616621 | Homozygous |
| F2 | 267 | Group D | 28.898722 | 40 | −11.101278 | Homozygous |
| G2 | 315 | Group D HET | 29.856798 | 31.415937 | −1.559139 | Heterozygous |
| H2 | 363 | Group D HET | 30.772238 | 30.318415 | 0.453823 | Heterozygous |
| A3 | 29 | Group D HET | 31.818707 | 29.703732 | 2.114975 | Heterozygous |
| B3 | 77 | CV9804 | 33.97833 | 40 | −6.02167 | Homozygous |
| C3 | 125 | CV9804 | 29.250994 | 38.0116 | −8.760606 | Homozygous |
| D3 | 173 | CV9804 | 29.335287 | 40 | −10.664713 | Homozygous |
| E3 | 221 | CV9804 HET | 31.243635 | 29.766205 | 1.47743 | Heterozygous |
| F3 | 269 | CV9804 HET | 31.18066 | 30.622314 | 0.558346 | Heterozygous |
| G3 | 317 | CV9804 HET | 30.902334 | 30.596828 | 0.305506 | Heterozygous |
| H3 | 365 | BW255-2 | 40 | 29.219034 | 10.780966 | Wildtype |
| A4 | 31 | BW255-2 | 40 | 29.1813 | 10.8187 | Wildtype |
| B4 | 79 | BW255-2 | 40 | 29.013493 | 10.986507 | Wildtype |
| C4 | 127 | Group B | 40 | 28.962784 | 11.037216 | Wildtype |
| D4 | 175 | Group B | 40 | 28.329138 | 11.670862 | Wildtype |
| E4 | 223 | Group B | 40 | 28.766186 | 11.233814 | Wildtype |
| F4 | 271 | UT-12-2 | 37.0332 | 37.246914 | −0.213714 | No DNA |
| G4 | 319 | UT-12-2 | 39.64275 | 36.364605 | 3.278145 | No DNA |
| H4 | 367 | UT-12-2 | 40 | 37.55851 | 2.44149 | No DNA |
| A5 | 33 | DIMI-39 | 39.767876 | 36.78326 | 2.984616 | No DNA |
| B5 | 81 | DIMI-39 | 37.09119 | 36.66263 | 0.42856 | No DNA |
| C5 | 129 | DIMI-39 | 36.86376 | 37.060997 | −0.197237 | No DNA |

LEGEND
dCt Cutoff between Null and Het   5
dCt Cutoff between Het and Homo  −5
WT-TET Cutoff                    39
HTt-FAM Cutoff                   39

Real-time assays using solutions with the forward primers TaAHASDMMFor2 (SEQ ID NO:16) and TaAHASDM-MFor3 (SEQ ID NO:18) provide dCt values which are sufficiently separated to ensure accurate zygosity calls and genotype designation between wild-type, heterozygous, and homozygous herbicide-tolerant. The TaAHASDMMFor2 forward primer (SEQ ID NO:16) shows tighter clustering in replicates and increases separation in dCt values between homozygous wild-type, heterozygous, and homozygous herbicide-tolerant samples over the TaAHASDMMFor3 forward primer (SEQ ID NO:18). Both the TaAHASDMMFor2 (SEQ ID NO:16) and TaAHASDMMFor3 (SEQ ID NO:18) can be used in assays to provide accurate zygosity calls and genotype designations.

Real-time assays using the solution with the forward primer TaAHASDForSNP (SEQ ID NO:19) provide dCt values which allow identification of the three genotype classes. However, the dCt values are close which can result in erroneous zygosity calls and genotype designations.

Real-time assays using solutions with the forward primers TaAHASBMMFor2 (SEQ ID NO:21) and TaAHASBMMFor3 (SEQ ID NO:23) provide dCt values which are comparable to the dCt values in assays using the TaAHASDMMFor2 (SEQ ID NO:16) and TaAHASDMMFor3 (SEQ ID NO:18), The TaAHASBMMFor2 (SEQ ID NO:21) and TaAHASBMMFor3 (SEQ ID NO:23) primers provide dCt values which are sufficiently separated to ensure accurate zygosity calls and genotype designation between wild-type, heterozygous, and homozygous herbicide-tolerant. The TaAHASBMMFor2 (SEQ ID NO:21) forward primer gives a two-fold higher average dCt between the heterozygous and homozygous herbicide-tolerant samples.

Real-time assays using the solution with the forward primer TaAHASBForSNP (SEQ ID NO:24) provides dCt values which allow identification of the three genotype classes. However, the dCt values are close which can result in erroneous zygosity calls and genotype designations.

Real-time assays using solutions with the forward primers TaAHASAMMFor2 (SEQ ID NO:26) and TaAHASAMMFor3 (SEQ ID NO:28) provide dCt values which are comparable to the dCt values in assays using the TaAHASDMMFor2 (SEQ ID NO: 16) and TaAHASDMMFor3 (SEQ ID NO:18). The TaAHASAMMFor2 (SEQ ID NO:26) and TaAHASAMMFor3 (SEQ ID NO:28) primers provide dCt values which are sufficiently separated to ensure accurate zygosity calls and genotype designation between wild-type, heterozygous, and homozygous herbicide-tolerant. These primers work equally well and can be used in assays to provide accurate zygosity calls and genotype designations.

Real-time assays using the solution with the forward primer TaAHASAForSNP (SEQ ID NO:29) provides dCt values which allow identification of the three genotype classes. However, the dCt values are close which can result in erroneous zygosity calls and genotype designations.

Real-time assays using the solution with the software-designed forward primer TaAHASD (SEQ ID NO:30) do not enable distinction between wild-type and heterozygous individuals for any of the AHASL genes.

Example 4

Real-Time Assay for AHASL of Wheat D Genome

A sample containing genomic DNA is obtained by any method known in the art for purifying genomic DNA from plant tissues, for example *Triticum aestivum*. Wheat genomic DNA can be obtained, for example, from young leaf tissue or seed flour. Samples can be obtained by extracting genomic DNA from bulk flour of wheat varieties representing, for example, S653N homozygous variants of the AHASL1D, AHASL1B, and AHASL genes of *T. aestivum* and AHASL and AHASL genes of *T. turgidum* ssp. *durum*.

When comparing two or more wheat plants, an equivalent amount of tissue from each plant can be used for the purification of the genomic DNA in order to ensure that samples from each of the plants will contain similar concentrations of genomic DNA. The DNA concentration of the sample is about 5-10 ng DNA per μL. While the method does not depend on a particular DNA concentration, the DNA concentration of the sample is preferably between about 5 and about 100 ng DNA per μL.

A stock solution of the TaAHASDMMFor2 primer (SEQ ID NO:16), is prepared to provide 25× concentrated mix according to the protocol of Example 3 and as shown in Table 1. The reverse AHASL primer (SEQ ID NO:31), AHASL wild-type probe (SEQ ID NO:32), and AHASL HT probe (SEQ ID NO:33) are included in each of the stock solutions. Each of the WheatDSNP mixes is stored at −20° C.

A polymerase mix ("Supplemented 2× Polymerase Mix") is prepared according to the protocol of Example 3 and as shown in Table 2. The Supplemented 2× Polymerase Mix is stored at 4° C.

A master mix for the real-time assay for the AHASL1D S653N is prepared from the Wheat DSNP mixes and Supplemented 2× Polymerase Mix according to the protocol of Example 3 and as shown in Table 3.

The real-time assay is conducted using a Biomek FxP according to the following protocol. 45 μl of 1× master mix is dispensed into each well of a strip of 8 tubes. The strip is placed on a designated 96 well plate rack with column 1 for quadrant 1, column 2 for quadrant 2, column 3 for quadrant 3, and column 4 for quadrant 4 of a 384 well PCR reaction plate. 3 μl of 'WheatDSNP' Real-time working master mix (1×) per well 2 μl DNA eluted in 1×TE per well (gDNA starting concentration is approximately 5-10 ng/μl). The plates are immediately sealed with optical sealing tape and are run for 2 minutes at 1000 rpm. The plates can be stored at 4° C. for up to 48 hours.

The plate is run on the light cycler under the cycling conditions according to the protocol of Example 3 and show in Table 4.

Zygosity call, genotype designations, and cutoff values are calculated according to the protocol in Example 3.

Figure 6:
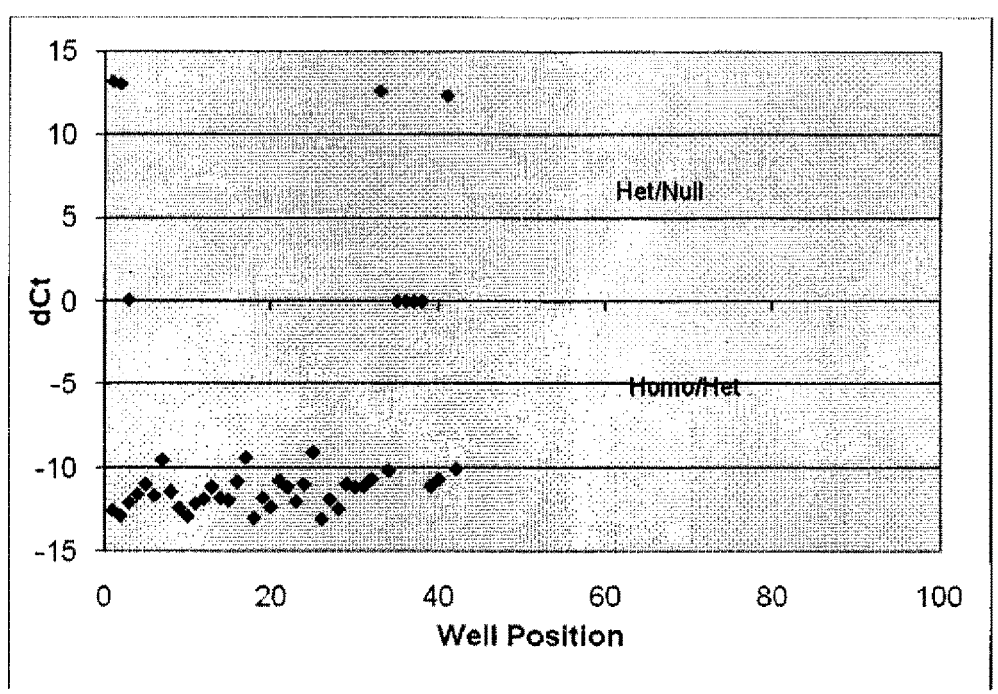
FIG. 6 is a scatter plot of dCt values of an experimental assay using the TaAHASDMMFor2 primer (SEQ ID NO:16).

Table 7 and its Legend provide results for an assay using the TaAHASDMMFor2 (SEQ ID NO:16) forward primer. FIG. 6 shows a scatter plot of the dCt values from assay results.

TABLE 7

| Assay | Sample ID | HT Ct | WT Ct | dCt | Zygosity Call (dCt Method) |
|---|---|---|---|---|---|
| 26 | Wildtype control | 40 | 26.84739 | 13.15261 | Wildtype |
| 74 | Wildtype control | 40 | 26.97574 | 13.02426 | Wildtype |
| 122 | Heterozygous control | 31.491217 | 31.42351 | 0.067707 | Heterozygous |
| 170 | Heterozygous control | 31.34674 | 31.652384 | −0.305644 | Heterozygous |
| 218 | Homozygous control | 29.99533 | 40 | −10.00467 | Homozygous |
| 266 | Homozygous control | 29.802464 | 40 | −10.197536 | Homozygous |
| 314 | | | | | |
| 362 | | | | | |
| 28 | 20212_1 | 28.347878 | 40 | −11.652122 | Homozygous |
| 76 | 20212_2 | 28.538382 | 40 | −11.461618 | Homozygous |
| 124 | 20212_3 | 27.452032 | 40 | −12.547968 | Homozygous |
| 172 | 20212_4 | 27.142103 | 40 | −12.857897 | Homozygous |
| 220 | 20212_5 | 27.91621 | 40 | −12.08379 | Homozygous |
| 268 | 20212_6 | 28.403366 | 40 | −11.596634 | Homozygous |
| 316 | 20212_7 | 28.981049 | 40 | −11.018951 | Homozygous |

TABLE 7-continued

| | | | | | |
|---|---|---|---|---|---|
| 364 | 20212_8 | 28.346386 | 40 | −11.653614 | Homozygous |
| 30 | 20212_1 | 30.446072 | 40 | −9.553928 | Homozygous |
| 78 | 20212_2 | 28.556992 | 40 | −11.443008 | Homozygous |
| 126 | 20212_3 | 27.556402 | 40 | −12.443598 | Homozygous |
| 174 | 20212_4 | 27.093315 | 40 | −12.906685 | Homozygous |
| 222 | 20212_5 | 27.8551 | 40 | −12.1449 | Homozygous |
| 270 | 20212_6 | 28.137955 | 40 | −11.862045 | Homozygous |
| 318 | 20212_7 | 28.819048 | 40 | −11.180952 | Homozygous |
| 366 | 20212_8 | 28.168386 | 40 | −11.831614 | Homozygous |
| 32 | 20212_9 | 28.063032 | 40 | −11.936968 | Homozygous |
| 80 | 20212_10 | 29.152721 | 40 | −10.847279 | Homozygous |
| 128 | 20216_1 | 30.606934 | 40 | −9.393066 | Homozygous |
| 176 | 20216_2 | 27.00255 | 40 | −12.99745 | Homozygous |
| 224 | 20216_3 | 28.186663 | 40 | −11.813337 | Homozygous |
| 272 | 20216_4 | 27.655886 | 40 | −12.344114 | Homozygous |
| 320 | 20216_5 | 29.225403 | 40 | −10.774597 | Homozygous |
| 368 | 20216_6 | 28.849354 | 40 | −11.150646 | Homozygous |
| 34 | 20212_9 | 27.97749 | 40 | −12.02251 | Homozygous |
| 82 | 20212_10 | 28.978636 | 40 | −11.021364 | Homozygous |
| 130 | 20216_1 | 30.920435 | 40 | −9.079565 | Homozygous |
| 178 | 20216_2 | 26.890776 | 40 | −13.109224 | Homozygous |
| 226 | 20216_3 | 28.095255 | 40 | −11.904745 | Homozygous |
| 274 | 20216_4 | 27.534174 | 40 | −12.465826 | Homozygous |
| 322 | 20216_5 | 29.027134 | 40 | −10.972866 | Homozygous |
| 370 | 20216_6 | 28.849108 | 40 | −11.150892 | Homozygous |
| 36 | 20216_7 | 28.879118 | 40 | −11.120882 | Homozygous |
| 84 | 20216_8 | 29.3099 | 40 | −10.6901 | Homozygous |
| 132 | 20216_9 | 40 | 27.394365 | 12.605635 | Wildtype |
| 180 | 20216_10 | 29.814688 | 40 | −10.185312 | Homozygous |
| 228 | empty | 40 | 40 | ND | No DNA |
| 276 | empty | 40 | 40 | ND | No DNA |
| 324 | empty | 40 | 40 | ND | No DNA |
| 372 | empty | 40 | 40 | ND | No DNA |
| 38 | 20216_7 | 28.879456 | 40 | −11.120544 | Homozygous |
| 86 | 20216_8 | 29.277208 | 40 | −10.722792 | Homozygous |
| 134 | 20216_9 | 40 | 27.689241 | 12.310759 | Wildtype |
| 182 | 20216_10 | 29.88885 | 40 | −10.11115 | Homozygous |

Legend
dCt Cutoff between Null and Het   5
dCt Cutoff between Het and Homo  −5
WT-TET Cutoff  39
HT-FAM Cutoff  39

While the foregoing disclosure has been described in some detail for purposes of clarity and understanding, it will be appreciated by one skilled in the art from a reading of this disclosure that various changes in form and detail can be made without departing from the true scope of the disclosure and appended claims.

What is claimed is:

1. A method for analyzing a plant AHASL gene, said method comprising:
   a) providing DNA comprising the plant AHASL gene;
   b) amplifying the DNA using an AHASL forward primer, an AHASL reverse primer, polymerase, and deoxyribonucleotide triphosphates;
   c) detecting products of the amplification with a wild-type AHASL probe and a herbicide-tolerant (HT) AHASL probe;
      wherein the AHASL forward primer is an oligonucleotide comprising a sequence selected from the group consisting of SEQ ID NO:16, SEQ ID NO:18, SEQ ID NO:21, SEQ ID NO:23, SEQ ID NO:26, and SEQ ID NO:28;
      and
      wherein wherein the wild-type AHASL probe is an oligonucleotide comprising the sequence set forth in SEQ ID NO:32 and the HT AHASL probe is an oligonucleotide comprising the sequence set forth in SEQ ID NO:33.

2. The method of claim 1 wherein said amplifying and detecting steps are conducted simultaneously in a real-time PCR assay.

3. The method of claim 1 wherein said detecting step identifies the AHASL gene as wild-type or variant for the single nucleotide polymorphism resulting in an amino acid substitution corresponding to the S653 (At)N substitution.

4. The method of claim 1 wherein said detecting step identifies the source of the plant AHASL gene.

5. The method of claim 4 wherein the source is a polyploid plant.

6. The method of claim 5 wherein the source is a wheat plant.

7. The method of claim 6 wherein the source is *Triticum aesivum* or *T. turgidum* ssp. *durum*.

8. The method of claim 6 wherein the source is *Triticum aesivum* or *T. turgidum* ssp. *durum*.

9. The method of claim 1 wherein said detecting step identifies the source genome of the plant AHASL gene.

10. The method of claim 9 wherein the source genome is a wheat A genome, a wheat B genome, or a wheat D genome.

11. The method of claim 1 wherein the plant AHASL gene is selected from the group consisting of a wheat AHASL1A gene, a wheat AHASL1B gene, and a wheat AHASL1D gene.

12. The method of claim 1 further comprising repeating said amplifying and detecting steps with a different AHASL forward primer comprising a sequence selected from the group consisting of SEQ ID NO:16, SEQ ID NO:18, SEQ ID NO:21, SEQ ID NO:23, SEQ ID NO:26, and SEQ ID NO:28 to identify the zygosity of the AHASL gene for the single nucleotide polymorphism resulting in an amino acid substitution corresponding to the S653(At)N substitution.

13. The method of claim 12 wherein said detecting steps identifies the source of the plant AHASL gene.

14. The method of claim 13 wherein the source is a polyploid plant.

15. The method of claim 14 wherein the source is a wheat plant.

16. The method of claim 1 wherein the AHASL forward primer is an oligonucleotide consisting of a sequence selected from the group consisting of SEQ ID NO:16, SEQ ID NO:18, SEQ ID NO:21, SEQ ID NO:23, SEQ ID NO:26, and SEQ ID NO:28.

17. The method of claim 1 wherein the AHASL reverse primer is an oligonucleotide having the sequence set forth in SEQ ID NO:31.

18. The method of claim 1 wherein the wild-type AHASL probe is labeled with a first type of detectable signal and the HT AHASL probe is labeled with a second type of detectable signal.

19. The method of claim 18 wherein the detectable signals are fluorescent reporter molecules.

20. The method of claim 1 wherein the DNA is genomic DNA.

21. The method of claim 20 wherein the DNA is obtained from a wheat plant.

22. The method of claim 21 wherein the wheat plant is a *Triticum aestivum*.

23. The method of claim 21 wherein the wheat plant is a *T. turgidum* ssp. *durum*.

* * * * *

SEQUENCE LISTING

```
<160> NUMBER OF SEQ ID NOS: 36

<210> SEQ ID NO 1
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Wild type AHASL1D
<221> NAME/KEY: CDS
<222> LOCATION: (1)...(42)

<400> SEQUENCE: 1 cac gtg ctg cct atg atc cca agc ggt ggt gct ttc aag gac           42
His Val Leu Pro Met Ile Pro Ser Gly Gly Ala Phe Lys Asp
1               5                   10

<210> SEQ ID NO 2
<211> LENGTH: 14
<212> TYPE: PRT
<213> ORGANISM: Triticum aestivum
```

-continued

<400> SEQUENCE: 2

His Val Leu Pro Met Ile Pro Ser Gly Gly Ala Phe Lys Asp
1               5                   10

<210> SEQ ID NO 3
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Variant AHASL1D
<221> NAME/KEY: CDS
<222> LOCATION: (1)...(42)

<400> SEQUENCE: 3 cac gtg ctg cct atg atc cca aac ggt ggt gct ttc aag gac      42
His Val Leu Pro Met Ile Pro Asn Gly Gly Ala Phe Lys Asp
1               5                   10

<210> SEQ ID NO 4
<211> LENGTH: 14
<212> TYPE: PRT
<213> ORGANISM: Triticum aestivum

<400> SEQUENCE: 4

His Val Leu Pro Met Ile Pro Asn Gly Gly Ala Phe Lys Asp
1               5                   10

<210> SEQ ID NO 5
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Wild type AHASL1B
<221> NAME/KEY: CDS
<222> LOCATION: (1)...(42)

<400> SEQUENCE: 5 cac gtg ctg cct atg atc cca agc ggt ggt gct ttt aag gac      42
His Val Leu Pro Met Ile Pro Ser Gly Gly Ala Phe Lys Asp
1               5                   10

<210> SEQ ID NO 6
<211> LENGTH: 14
<212> TYPE: PRT
<213> ORGANISM: Triticum aestivum

<400> SEQUENCE: 6

His Val Leu Pro Met Ile Pro Ser Gly Gly Ala Phe Lys Asp
1               5                   10

<210> SEQ ID NO 7
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Variant AHASL1B
<221> NAME/KEY: CDS
<222> LOCATION: (1)...(42)

<400> SEQUENCE: 7

```
cac gtg ctg cct atg atc cca aac ggt ggt gct ttt aag gac          42
His Val Leu Pro Met Ile Pro Asn Gly Gly Ala Phe Lys Asp
1               5                  10
```

<210> SEQ ID NO 8
<211> LENGTH: 14
<212> TYPE: PRT
<213> ORGANISM: Triticum aestivum

<400> SEQUENCE: 8

```
His Val Leu Pro Met Ile Pro Asn Gly Gly Ala Phe Lys Asp
1               5                  10
```

<210> SEQ ID NO 9
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Wild type AHASL1A
<221> NAME/KEY: CDS
<222> LOCATION: (1)...(42)

<400> SEQUENCE: 9

```
cac gtg ctg cct atg atc cca agc ggt ggt gct ttc aag gac          42
His Val Leu Pro Met Ile Pro Ser Gly Gly Ala Phe Lys Asp
1               5                  10
```

<210> SEQ ID NO 10
<211> LENGTH: 14
<212> TYPE: PRT
<213> ORGANISM: Triticum aestivum

<400> SEQUENCE: 10

```
His Val Leu Pro Met Ile Pro Ser Gly Gly Ala Phe Lys Asp
1               5                  10
```

<210> SEQ ID NO 11
<211> LENGTH: 42
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: Variant AHASL1A
<221> NAME/KEY: CDS
<222> LOCATION: (1)...(42)

<400> SEQUENCE: 11

```
cac gtg ctg cct atg atc cca aac ggt ggt gct ttc aag gac          42
His Val Leu Pro Met Ile Pro Asn Gly Gly Ala Phe Lys Asp
1               5                  10
```

<210> SEQ ID NO 12
<211> LENGTH: 14
<212> TYPE: PRT
<213> ORGANISM: Triticum aestivum

<400> SEQUENCE: 12

```
His Val Leu Pro Met Ile Pro Asn Gly Gly Ala Phe Lys Asp
1               5                  10
```

```
<210> SEQ ID NO 13
<211> LENGTH: 26
<212> TYPE: DNA
<213> ORGANISM: Artificial Sequence
<220> FEATURE:
<223> OTHER INFORMATION: Primer TaAHASMMFor2

<400> SEQUENCE: 13
cagggccata cttgttggat atdath                                          26

<210> SEQ ID NO 14
<211> LENGTH: 23
<212> TYPE: DNA
<213> ORGANISM: Artificial Sequence
<220> FEATURE:
<223> OTHER INFORMATION: Primer TaAHASMMFor3

<400> SEQUENCE: 14
ggccatactt gttggatatd ath                                             23

<210> SEQ ID NO 15
<211> LENGTH: 26
<212> TYPE: DNA
<213> ORGANISM: Artificial Sequence
<220> FEATURE:
<223> OTHER INFORMATION: Primer TaAHASDMMFor2Gen

<400> SEQUENCE: 15
cagggccata cttgttggat atdata                                          26

<210> SEQ ID NO 16
<211> LENGTH: 26
<212> TYPE: DNA
<213> ORGANISM: Artificial Sequence
<220> FEATURE:
<223> OTHER INFORMATION: Primer TaAHASDMMFor2

<400> SEQUENCE: 16
cagggccata cttgttggat ataata                                          26

<210> SEQ ID NO 17
<211> LENGTH: 23
<212> TYPE: DNA
<213> ORGANISM: Artificial Sequence
<220> FEATURE:
<223> OTHER INFORMATION: Primer TaAHASDMMFor3Gen

<400> SEQUENCE: 17
ggccatactt gttggatatc bta                                             23

<210> SEQ ID NO 18
<211> LENGTH: 23
<212> TYPE: DNA
<213> ORGANISM: Artificial Sequence
<220> FEATURE:
<223> OTHER INFORMATION: Primer TaAHASDMMFor3

<400> SEQUENCE: 18
ggccatactt gttggatatc gta                                             23

<210> SEQ ID NO 19
<211> LENGTH: 26
<212> TYPE: DNA
<213> ORGANISM: Artificial Sequence
<220> FEATURE:
<223> OTHER INFORMATION: Primer TaAHASDForSNP
```

<400> SEQUENCE: 19
cagggccata cttgttggat atcata                                          26

<210> SEQ ID NO 20
<211> LENGTH: 26
<212> TYPE: DNA
<213> ORGANISM: Artificial Sequence
<220> FEATURE:
<223> OTHER INFORMATION: Primer TaAHASBMMFor2Gen

<400> SEQUENCE: 20
cagggccata cttgttggat atdatt                                          26

<210> SEQ ID NO 21
<211> LENGTH: 26
<212> TYPE: DNA
<213> ORGANISM: Artificial Sequence
<220> FEATURE:
<223> OTHER INFORMATION: Primer TaAHASBMMFor2

<400> SEQUENCE: 21
cagggccata cttgttggat ataatt                                          26

<210> SEQ ID NO 22
<211> LENGTH: 23
<212> TYPE: DNA
<213> ORGANISM: Artificial Sequence
<220> FEATURE:
<223> OTHER INFORMATION: Primer TaAHASBMMFor3Gen

<400> SEQUENCE: 22
ggccatactt gttggatatd att                                             23

<210> SEQ ID NO 23
<211> LENGTH: 23
<212> TYPE: DNA
<213> ORGANISM: Artificial Sequence
<220> FEATURE:
<223> OTHER INFORMATION: Primer TaAHASBMMFor3

<400> SEQUENCE: 23
ggccatactt gttggatatg att                                             23

<210> SEQ ID NO 24
<211> LENGTH: 26
<212> TYPE: DNA
<213> ORGANISM: Artificial Sequence
<220> FEATURE:
<223> OTHER INFORMATION: Primer TaAHASBForSNP

<400> SEQUENCE: 24
cagggccata cttgttggat atcatt                                          26

<210> SEQ ID NO 25
<211> LENGTH: 26
<212> TYPE: DNA
<213> ORGANISM: Artificial Sequence
<220> FEATURE:
<223> OTHER INFORMATION: Primer TaAHASAMMFor2Gen

<400> SEQUENCE: 25
cagggccata cttgttggat atdatc                                          26

```
<210> SEQ ID NO 26
<211> LENGTH: 26
<212> TYPE: DNA
<213> ORGANISM: Artificial Sequence
<220> FEATURE:
<223> OTHER INFORMATION: Primer TaAHASAMMFor2

<400> SEQUENCE: 26
cagggccata cttgttggat ataatc                                         26

<210> SEQ ID NO 27
<211> LENGTH: 23
<212> TYPE: DNA
<213> ORGANISM: Artificial Sequence
<220> FEATURE:
<223> OTHER INFORMATION: Primer TaAHASAMMFor3Gen

<400> SEQUENCE: 27
ggccatactt gttggatatd atc                                            23

<210> SEQ ID NO 28
<211> LENGTH: 23
<212> TYPE: DNA
<213> ORGANISM: Artificial Sequence
<220> FEATURE:
<223> OTHER INFORMATION: Primer TaAHASAMMFor3

<400> SEQUENCE: 28
ggccatactt gttggatata atc                                            23

<210> SEQ ID NO 29
<211> LENGTH: 26
<212> TYPE: DNA
<213> ORGANISM: Artificial Sequence
<220> FEATURE:
<223> OTHER INFORMATION: Primer TaAHASAForSNP

<400> SEQUENCE: 29
cagggccata cttgttggat atcatc                                         26

<210> SEQ ID NO 30
<211> LENGTH: 17
<212> TYPE: DNA
<213> ORGANISM: Artificial Sequence
<220> FEATURE:
<223> OTHER INFORMATION: Primer TaAHASD

<400> SEQUENCE: 30
tcccgcatca ggagcac                                                   17

<210> SEQ ID NO 31
<211> LENGTH: 21
<212> TYPE: DNA
<213> ORGANISM: Artificial Sequence
<220> FEATURE:
<223> OTHER INFORMATION: Reverse Primer

<400> SEQUENCE: 31
gcgcatgtca cacttgtagg t                                              21

<210> SEQ ID NO 32
<211> LENGTH: 15
<212> TYPE: DNA
<213> ORGANISM: Artificial Sequence
<220> FEATURE:
<223> OTHER INFORMATION: wild-type Probe
```

<400> SEQUENCE: 32
tatgatccca agcgg                                                    15

<210> SEQ ID NO 33
<211> LENGTH: 15
<212> TYPE: DNA
<213> ORGANISM: Artificial Sequence
<220> FEATURE:
<223> OTHER INFORMATION: herbicide-tolerant Probe

<400> SEQUENCE: 33
tatgatccca aacgg                                                    15

<210> SEQ ID NO 34
<211> LENGTH: 983
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1D

<400> SEQUENCE: 34
tttggtccat ggcacaagga gttggatcag cagaagaggg agtttcctct aggattcaag    60
acttttggcg aggccatccc gccgcaatat gctatccagg tactggatga gctgacaaaa   120
ggggaggcga tcattgccac tggtgttggg cagcaccaga tgtgggcggc tcagtattac   180
acttacaagc ggccacggca gtggctgtct tcgtctggtt tgggggcaat gggatttggg   240
ttaccagctg cagctggcgc tgctgtggcc aacccaggtg ttacagttgt tgacattgat   300
ggtgatggta gtttcctcat gaacattcag gagttggcgt tgatccgcat tgagaacctc   360
ccagtgaagg tgatgatatt gaacaaccag catctgggaa tggtggtgca gtgggaggat   420
aggttttaca aggccaatcg ggcgcacaca taccttggca acccagaaaa tgagagtgag   480
atatatccag attttgtgac gattgctaaa ggattcaacg ttccagcagt tcgagtgacg   540
aagaagagcg aagtcactgc agcaatcaag aagatgcttg acccccagg gccatacttg   600 ttggatatca tagtcccgca tcaggagcac gtgctgccta tgatcccaag cggtggtgct   660
ttcaaggaca tgatcatgga gggtgatggc aggacctcgt actgaaattt cgacctacaa   720
gacctacaag tgtgacatgc gcaatcagca tgatgcccgc gtgttgtatc aactactagg   780
ggttcaactg tgarccatgc gttttctagt ttgcttgttt cattcatata agcttgtrtt   840
acttagttcc gaaccctgta gttttgtagt ctatgttctc ttttgtaggg atgtgctgtc   900
ataaratrtc atgcaagttt cttgtcctac atatcaataa taagtacttc catgcagtaa   960
aaaaaaaaaa aaaaaaaaaa aaa                                          983

<210> SEQ ID NO 35
<211> LENGTH: 983
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1B

<400> SEQUENCE: 35
tttggtccat ggcacaagga gttggatcag cagaagaggg agtttcctct aggattcaag    60
acttttggtg aggccatccc gccgcaatat gctatccagg tactggatga gctgacaaaa   120
ggggaggcga tcattgccac cggtgttggg cagcatcaga tgtgggcggc tcagtattac   180

```
acttacaagc ggccacggca gtggctgtct tcatccggtt tgggtgcaat gggatttggg       240
ttgccagctg cagctggcgc tgctgtggcc aacccaggtg ttacagttgt tgacattgat       300
ggggatggta gtttcctcat gaacattcag gagttggcgt tgatccgtat tgagaacctc       360
ccagtgaagg tgatgatatt gaacaaccag catctgggaa tggtggtgca gtgggaggat       420
aggttttaca aggccaaccg ggcgcacaca taccttggca acccagaaaa tgagagtgag       480
atatatccag attttgtgac gattgctaaa ggattcaacg ttccggcagt tcgtgtgacg       540
aagaagagcg aagtcactgc agcaatcaag aagatgcttg agaccccagg gccatacttg       600
ttggatatca ttgtcccgca tcaggagcac gtgctgccta tgatcccaag cggtggtgct       660
tttaaggaca tgatcatgga gggtgatggc aggacctcgt actgaaattt cgacctacaa       720
gacctacaag tgtgacatgc gcaatcagca tgataccvgc gtgttgtatc aactactggg       780
ggttcaactg tgaaccatgc gttttctagt ttgcttgttt cattcatata agcttgtgtt       840
acttagttcc gaaccgtgta gttttgtagt ctctgttctc ttttgtaggg aygtgctgtc       900
ataaratatc atgcaagttt cttgtcctac atatcaataa taagcacttc catggagcaa       960
aaaaaaaaaa aaaaaaaaaa aaa                                              983

<210> SEQ ID NO 36
<211> LENGTH: 983
<212> TYPE: DNA
<213> ORGANISM: Triticum aestivum
<220> FEATURE:
<221> NAME/KEY: misc_feature
<222> LOCATION: (0)...(0)
<223> OTHER INFORMATION: AHASL1A

<400> SEQUENCE: 36
tttggtccat ggcacaagga gttggatcag cagaagaggg agtttcctct aggattcaag        60
acttttggcg aggccatccc gccgcaatat gctatccagg tactggatga gctgacaaaa       120
ggggaggcga tcattgctac tggtgttggg cagcaccaga tgtgggcggc tcagtattac       180
acttacaagc ggccacggca gtggctgtct tcgtctggtt tgggggcaat gggatttggg       240
ttaccagctg cagctggcgc tgctgtggcc aacccaggtg ttacagttgt tgacattgat       300
ggagatggta gtttcctcat gaacattcag gagttggcat tgatccgtat tgagaacctc       360
cctgtgaagg tgatgatatt gaacaaccag catctgggaa tggtggtgca atgggaggat       420
aggttttaca aggccaatcg ggcgcacaca taccttggca acccagaaaa tgagagtgag       480
atatatccag attttgtgac gattgctaaa ggattcaacg ttccggcagt tcgtgtgacg       540
aagaagagcg aagtcactgc agcaatcaag aagatgcttg agaccccagg gccatacttg       600
ttggatatca tcgtcccgca tcaggagcac gtgctgccta tgatcccaag cggtggtgct       660
ttcaaggaca tgatcatgga gggtgatggc aggacctcgt actgaaattt cgacctacaa       720
gacctacaag tgtgacatgc gcaatcagca tggtgcccgc gtgttgtatc aactactagg       780
ggttcaactg tgaaccatgc gttttctagt ttgcttgttt cattcatata agcttgtgtt       840
acttagttcc gaaccctgta gctttgtagt ctatgctatc ttttgtaggg atgtgctgtc       900
ataaaatatc atgcaagttt cttgtcctac atatcaataa taagtacttc catggaaaaa       960
aaaaaaaaaa aaaaaaaaaa aaa                                              983
```